United States Patent [19]

Duncan et al.

[11] Patent Number: 5,965,118
[45] Date of Patent: Oct. 12, 1999

[54] POLYMER-PLATINUM COMPOUNDS

[75] Inventors: Ruth Duncan; Evagoras G. Evagorou, both of London; Robert G. Buckley, Reading; Elisabetta Gianasi, London, all of United Kingdom

[73] Assignee: Access Pharmaceuticals, Inc., Dallas, Tex.

[21] Appl. No.: 09/060,455

[22] Filed: Apr. 14, 1998

Related U.S. Application Data

[60] Provisional application No. 60/044,743, Apr. 18, 1997.

[51] Int. Cl.$^6$ .......................... A61K 31/78; A61K 33/24; C07K 5/103; C08F 8/42
[52] U.S. Cl. .......................... 424/78.27; 424/649; 514/6; 525/54.1; 530/330; 530/345
[58] Field of Search .................. 525/54.1; 526/238.1; 424/1.69, 78.26, 78.27, 649; 530/330, 331, 345; 514/6

[56] References Cited

U.S. PATENT DOCUMENTS

| | | | |
|---|---|---|---|
| 4,062,831 | 12/1977 | Kopecek et al. | 526/208 |
| 4,097,470 | 6/1978 | Drobnik et al. | 526/16 |
| 4,931,553 | 6/1990 | Gill et al. | 536/121 |
| 5,037,883 | 8/1991 | Kopecek et al. | 525/54.1 |
| 5,362,831 | 11/1994 | Mongelli et al. | 526/304 |
| 5,420,105 | 5/1995 | Gustavson et al. | 514/2 |
| 5,473,055 | 12/1995 | Mongelli et al. | 530/329 |
| 5,547,667 | 8/1996 | Angelucci et al. | 424/181.1 |
| 5,569,720 | 10/1996 | Mongelli et al. | 525/329.4 |

FOREIGN PATENT DOCUMENTS

| | | |
|---|---|---|
| 187547 B1 | 7/1986 | European Pat. Off. |
| 190464 A2 | 8/1986 | European Pat. Off. |
| WO 88/00837 | 2/1988 | WIPO |
| WO 92/10212 | 6/1992 | WIPO |
| WO 93/13804 | 7/1993 | WIPO |
| WO 94/02106 | 2/1994 | WIPO |
| WO 94/07536 | 4/1994 | WIPO |
| WO 97/12891 | 4/1997 | WIPO |

OTHER PUBLICATIONS

Bogdanov, A.A., et al., "An Adduct of cis–Diamminedichloroplatinum(II) and poly(ethylene glycol)poly(L–lysine-)–Succinate: Synthesis and Cytotoxic Properties," Bioconjugate Chem. 7: 144–149 (1996).

Duncan, R., et al., "The role of polymer conjugates in the diagnosis and treatment of cancer," S.T.P. Pharma Sciences 6(4):237–263 (1996).

Duncan, Ruth, "Drug–polymer conjugates: potential for improved chemotherapy," Anti–Cancer Drugs #:175–210 (1992).

Duncan, R., et al., "Anticancer agents coupled to N–(2–hydroxypropyl)methacrylamide copolymers. I. Evaluation of daunomycin and puromycin conjugates in vitro," Br. J. Cancer 55:165–174 (1987).

Fiebig, H.H., et al., "GB–21, a novel platinum polymer with antitumor activity in human renal and mammary xenografts," Proceedings of the American Association for Cancer Research 37:297 Abstract No. 2021 (1996).

Filipová–Vopršálová, Marie, et al., "Biodistribution of trans–1,2–diaminocyclohexane–trimellito–platinum(II) attached to macromolecular carriers I. Poly (hydroxyethyl–D,L–asparagine) carrier," Journal of Controlled Release 17: 89–98 (1991).

Fujii, K., et al., "Control of Pharmacokinetics and Nephrotoxicity of cis–DDP by Alginate," Proceed. Intern. Symp. Control. Rel. Bioact. Mater. 23: 639–640 (1996).

(List continued on next page.)

*Primary Examiner*—Jeffrey E. Russel
*Attorney, Agent, or Firm*—Judy M. Mohr; Dehlinger & Associates

[57] ABSTRACT

A polymer-platinum compound for use in tumor treatment is described. The compound is composed of a polymer backbone having platinum-containing side chains spaced along the polymer backbone. The side chains are composed of an oligopeptide attached at one end to the backbone and at the other end to the platinum compound.

24 Claims, 15 Drawing Sheets

OTHER PUBLICATIONS

Han, Man Jung, et al., "Synthesis and Antitumor Activity of Polyanion–Pt–Complexes Containing Alicyclic Amines as Ligands," Journal of Bioactive and Compatible Polymers 9: 142–151 (1994).

Johnsson, A., et al., "A topographic study on the distribution of cisplatin in xenografted tumors on nude mice," Anti–Cancer Drugs 7: 70–77 (1996).

Neuse, E.W., et al., "Carrier Polymers for Cisplatin–type Anticancer Drug Models," *Polymers for Advanced Technologies* vol. 7, John Wiley & Sons, Ltd, pp. 867–872, 1996.

Neuse, E.W., et al., "cis–Diaminedichloroplatinum(II) Complexes Reversibly Bound to Water–Soluble Polyaspartamide Carriers for Chemotherapeutic Applications. II: Platinum Coordination to Ethylenediamine Ligands Attached to Poly-(ethylene oxide)–Grafted Carrier Polymers," Journal of Inorganic and Organometallic Polymers 5(3): 195–207 (1995).

Schechter, B., et al., "Soluble Polymers as Carriers of Cis–Platinum," Journal of Controlled Release 10: 75–87 (1989).

Seymour, L.W., et al., "Effect of molecular weight ($M_w$) of N–(2–hydroxypropyl)methacrylamide copolymers on body distribution and rate of excretion after subcutaneous, intraperitoneal, and intravenous administration to rats," Journal of Biomedical Materials Research 21: 1341–1358 (1987).

Sohn, Youn Soo, et al., "Synthesis and antitumor activity of novel polysphosphazene–(diamine) platinum (II)," Int. J. Pharm 153:79–91 (1997).

Sohn, Youn Soo, et al., "A novel polymeric platinum (II) anticancer agent KI 30606. Preclinic studies of a water-–soluble polyphosphazene–Pt (DACH) conjugate," Abstract No. 118, Conference Proceedings (Not dated).

Neuse, E.W., et al., "cis–Diaminedichloroplatinum(II) Complexes Reversibly Bound to Water–Soluble Polyasparatamide Carriers for Chemotherapeutic Applications. I. Platinum Coordination to Preformed Carrier–Attached Ethylenediamine Ligands," J. Inorg. Organomet. Polym. 1(2): 147–165 (1991).

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
       (A) LENGTH: 2 amino acids
       (B) TYPE: amino acid
       (C) STRANDEDNESS: single
       (D) TOPOLOGY: linear (xi) SEQUENCE DESCRIPTION: SEQ ID NO:1:

Gly Gly
 1

(2) INFORMATION FOR SEQ ID NO:2:

(i) SEQUENCE CHARACTERISTICS:
       (A) LENGTH: 3 amino acids

```
        (B) TYPE: amino acid
        (C) STRANDEDNESS: single
        (D) TOPOLOGY: linear (xi) SEQUENCE DESCRIPTION: SEQ ID NO:2:

Gly Phe Gly
 1

(2) INFORMATION FOR SEQ ID NO:3:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:3:

Gly Phe Phe
 1

(2) INFORMATION FOR SEQ ID NO:4:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:4:

Gly Leu Gly
 1

(2) INFORMATION FOR SEQ ID NO:5:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:5:

Gly Val Ala
 1

(2) INFORMATION FOR SEQ ID NO:6:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:6:

Gly Phe Ala
 1

(2) INFORMATION FOR SEQ ID NO:7:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:7:

Gly Leu Phe
 1
```

-continued (2) INFORMATION FOR SEQ ID NO:8:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:8:

Gly Leu Ala
1

(2) INFORMATION FOR SEQ ID NO:9:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:9:

Ala Val Ala
1

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:10:

Gly Phe Leu Gly
1

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:11:

Gly Phe Phe Leu
1

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:12:

Gly Leu Leu Gly
1

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:13:

```
Gly Phe Tyr Ala
1
```

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:14:

```
Gly Phe Gly Phe
1
```

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:15:

```
Ala Gly Val Phe
1
```

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:16:

```
Gly Phe Phe Gly
1
```

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:17:

```
Gly Phe Leu Gly Phe
1               5
```

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:18:

```
Gly Gly Phe Leu Gly Phe
1               5
```

POLYMER-PLATINUM COMPOUNDS

This application claims the priority of U.S. provisional application Ser. No. 60/044,743, filed Apr. 18, 1997, which is incorporated herein by reference.

FIELD OF THE INVENTION

The present invention relates to a polymer-platinum compound for use in tumor treatment.

REFERENCES

Bogdanov, Jr., A. A., et al., *Bioconjugate Chem.* 7:144–149 (1996).
Duncan, R., et al., *Brit. J. Cancer* 55:165–174 (1987).
Duncan, R., et al., *Anti-Cancer Drugs* 3:175–210 (1992).
Fiebig, H. H., et al., *Proc. Am. Asso. for Cancer Res.* 37:297, Abstract No. 2021 (1996).
Filipová-Vosprsálová, M., et al., *J. Controlled Release* 17(89–98) (1991).
Freise, J., et al., *Arch. Int. Pharmacodyn.* 258:180–192 (1982).
Fuji, K., et al., *Proc. Intern. Symp. Control. Rel. Bioact. Mater.* 23:639–640 (1996).
Han, M. J., et al., *J. Bioact. and Biocompat. Polymers* 9:142 (1994).
Johnsson, A., and Cavallin-Ståhl, E., *Anti-Cancer Drugs* 7:70–77 (1996).
Neuse, E. W., et al., *J. Inorganic and Organometallic Polymer* 5(3):195–207 (1995).
Prestayko, A. W., *CANCER AND CHEMO. VOL III* (Crooke, et al., Eds.) Academic Press, NY, 133–154 (1981).
Schechter, B., et al., *J. Controlled Release* 10:75–87 (1989).
Seymour, L. W., et al., *J. of Biomed. Mat. Res.* 21:1341–1358 (1987).
Steerenberg, P. A., et al, *International Journal of Pharmaceutics* 40:51–62 (1987).
Sur, B., et al, *Oncology* 40:372–376 (1983).
Weiss, R. B., et al., *Drugs* 46(3):360–377 (1993).

BACKGROUND OF THE INVENTION

Cis-diaminedichloroplatinum(II) (cisplatin) is widely used in cancer chemotherapy for treatment of solid tumors, including ovarian, testicular and head and neck, and is especially effective in combined chemotherapy against squamous cell carcinoma and small cell lung carcinoma (Sur, et al., 1983; Steerenberg, et al., 1987).

Antitumor activity of cisplatin results from the ability of the diaquo species to crosslink the N-7 guanine residue of DNA producing intrastrand and interstrand crosslinks. To display antitumor activity, platinum complexes require two cis amine or ammine functionalities having at least one hydrogen atom that will hydrogen-bond to the oxygen atoms of the DNA phosphate groups and two strongly-bound leaving groups, e.g., chloride.

Like other cancer chemotherapeutic agents, cisplatin is a highly toxic drug. The main disadvantages of cisplatin are its extreme nephrotoxicity, which is the main dose-limiting factor, its rapid excretion via the kidneys, with a circulation half life of only a few minutes, and its strong affinity to plasma proteins (Freise, et al., 1982).

Attempts to minimize the toxicity of the drug have included combination chemotherapy, synthesis of cisplatin analogues (Prestayko, 1991; Weiss, et al., 1993), immunotherapy and entrapment in liposomes (Sur, et al., 1983; Weiss, et al., 1993) and preparation of polymer-platinate conjugates (Bogdanov, Jr., et al., 1996; Filipová-Voprsálová, et al., 1991; Fuji, et al., 1996; Han, et al., 1994; Johnsson and Cavallin-Ståhl, 1996; Fiebig, et al., 1996; Neuse, et al., 1995; Schechter, et al., 1989).

With respect to the synthesis of cisplatin analogues, numerous platinum analogues have undergone preclinical and clinical trials, however only cisplatin and carboplatin have been approved for routine clinical use (Prestayko, 1991; Weiss, et al., 1993). Many of the analogues show no significant improvement in therapeutic index when compared to cisplatin. Cisplatin and its analogues have other drawbacks. Many are inactive when administered orally, some have low solubility in water and most induce severe toxic side effects including renal disfunction, nausea and vomiting, myelosuppression and neurotoxicity.

With respect to the preparation of polymer-platinum conjugates, such conjugates have been proposed as an approach to increasing solubility and reducing systemic toxicity. Although several platinum-polymer systems have been reported (Bogdanov, Jr., et al., 1996; Filipová-Voprsálová, et al., 1991; Fuji, et al., 1996; Han, et al., 1994; Johnsson and Cavallin-Ståhl, 1996; Fiebig, et al., 1996; Neuse, et al., 1995; Schechter, et al., 1989) none have so far entered clinical investigation and few have displayed significant benefit in vivo. Failure has been due to lack of biocompatibility, toxicity of the proposed carrier, lack of antitumor activity and other problems.

SUMMARY OF THE INVENTION

Accordingly, it is an object of the invention to provide new polymer-platinum compounds having antitumor activity in vivo.

In one aspect, the invention includes a composition for use in tumor treatment, comprising polymer-platinum compounds designed to accumulate at a tumor site. The compound is composed of a synthetic polymer backbone having platinum-containing side chains spaced along the backbone. The side chains (i) are composed of an oligopeptide attached at one end to the backbone and at the other end to a platinum compound and (ii) include at least one linkage which is designed to be cleaved under selected physiological conditions to yield the platinum compound which has, or is converted in vivo to have, anti-tumor activity.

In one embodiment, the synthetic polymer is a homopolymer of an N-alkyl acrylamide having a molecular weight of between about 1,000–5,000,000 daltons.

In another embodiment, the synthetic polymer is a copolymer having a molecular weight between 1,000–5,000,000 daltons and contains two repeat units m and n in a ratio m:n of between about 0.1–99.9.

The repeat units, in one embodiment, are composed of an N-alkyl acrylamide unit and of a unit carrying the oligopeptide side chain which terminates in a proximal end group capable of attaching the platinum compound.

In one embodiment, the polymer in the polymer-platinum compound is a copolymer of the form:

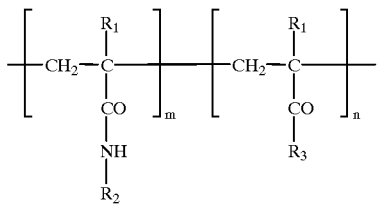

where $R_1$ is H or $CH_3$, $R_2$ is a lower alkyl or lower hydroxyalkyl group, and $R_3$ is a oligopeptide side chain.

The oligopeptide is, in another embodiment, an oligopeptide of the form Gly-$(W)_p$-Gly where p can be 0 to 3 and (W) can be any amino acid or combination of any amino acid. In one embodiment, the peptide is Gly-Phe-Leu-Gly (SEQ ID NO:10) and terminates in a carboxyl, diamine or malonyl moiety for attachment to the platinum compound. In another embodiment, the peptide is Gly-Gly (SEQ ID NO:1) terminating in a proximal carboxyl end group.

In a preferred embodiment, $R_1$ is $CH_3$, $R_2$ is 2-hydroxypropyl, and $R_3$ is Gly-Phe-Leu-Gly-[X] (SEQ ID NO:10) where [X] is a diamine, a carboxyl group or a malonyl moiety.

The polymer-platinum compound is dissolved in a pharmaceutically acceptable medium suitable for parenteral administration.

In another aspect, the invention includes a method of targeting a platinum compound to a solid tumor in a subject. The method includes preparing a polymer-platinum compound composed of a synthetic polymer backbone having side chains spaced along the backbone. The side chains (i) are composed of an oligopeptide attached at one end to the backbone and at the other end to a platinum compound and (ii) include at least one linkage which is designed to be cleaved under selected physiological conditions to yield the platinum compound which has, or is converted in vivo to have, anti-tumor activity. The compound is parenterally administered in a pharmaceutically effective amount to the subject.

In another aspect, the invention includes a method of enhancing the therapeutic index of a platinum compound, when the compound is used for treating a tumor by administering parenterally a pharmaceutically acceptable solution containing the compound to a subject. The method includes, prior to administering the compound, complexing the platinum compound with a copolymer composed of an N-alkyl acrylamide first repeat unit and a second repeat unit having an oligopeptide side chain which terminates in a proximal end group capable of complexing with the platinum compound.

In another aspect, the invention includes a method of improving the solubility and/or stability of a platinum compound by complexing the compound with a copolymer composed of an N-alkyl acrylamide first repeat unit and a second repeat unit having an oligopeptide side chain which terminates in a proximal end group capable of complexing with said platinum compound. The polymer-platinum complex is more soluble and/or more stable under physiological conditions than non-complex platinum compounds.

These and other objects and features of the invention will be more fully appreciated when the following detailed description of the invention is read in conjunction with the accompanying drawings.

DETAILED DESCRIPTION OF THE INVENTION

I. Preparation of the Polymer-Platinum Compound

Figure 1A:
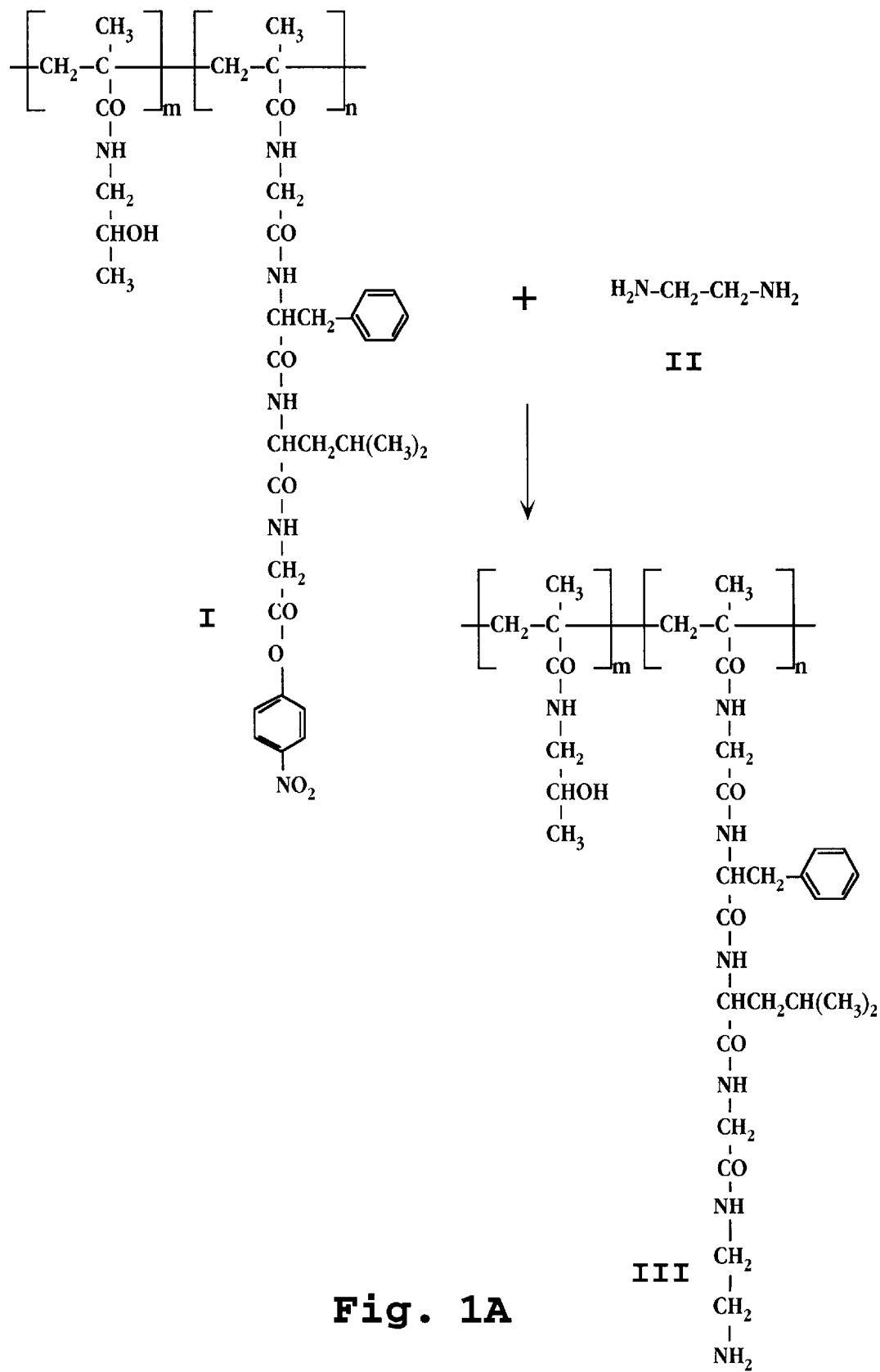
FIGS. 1A–1B are reaction schemes for synthesis of a hydroxypropyl methylacrylamide (HPMA) copolymer carrying an oligopeptide side chain with an ethylenediamine end group, where the oligopeptide is Gly-Phe-Leu-Gly (SEQ ID NO:10) (FIG. 1A) or Gly-Gly (SEQ ID NO:1) (FIG, 1B)

The polymer-platinum compound of the present invention includes a polymer for attachment of a platinum compound. As referred to herein, "platinum", typically used in the context of a platinum complex or compound, refer to a platinum metal atom bound to one or more ligands. The platinum atom may carry a formal charge, such as in the case of platinum salts such as $K_2PtCl_4$, potassium tetrachloroplatinate, in which the platinum carries a formal charge of (−2), or may carry no formal charge, as in cisplatin, $PtCl_2(NH_3)_2$. The platinum metal atom may exist in various oxidation states, such as Pt(0), Pt(II), or Pt(IV), although platinum, in the context of the present invention, is typically Pt(II). The platinum species can be in any coordination state, but is typically four-coordinate.

"Platinate" or "platinate species", as used herein, refers to a platinum compound in which the platinum atom is in an oxidation state of Pt(II) or Pt(IV).

A variety of polymers are suitable for use and generally include any polymer that is biocompatible, e.g., non-toxic and non-immunogenic. Preferably, the polymer is synthetic, to readily adjust the molecular weight range to achieve a size appropriate for enhanced endothelial permeation and retention at a tumor site and for renal filtration. Preferred polymers are hydrophilic for ease in preparation of a pharmaceutic and more preferably the polymer is water soluble. The polymer should also be stable, and, in particular, stable after preparation of the polymer-platinum compound and formulation into a pharmaceutical preparation.

Polymers suitable for in vivo administration and for conjugation with drugs have been reviewed by Duncan (Duncan, et al., 1992). Such polymers, which also are suitable for use in the present invention include, polyvinylpyrrolidone, polyethyleneglycol and copolymers thereof, dextrans, methacrylate-vinylpyrrolidone copolymers and others. It will be appreciated that the selected polymer can be derivatized with chemical moieties suitable for attaching the platinum compound.

The polymer can be a homopolymer or a copolymer, including block copolymers, random copolymers and alternating copolymers. The polymer can be crosslinked if desired with non-degradable or bio-degradable linkages to achieve desired physical properties. One preferred family of polymers for use in the present invention are N-alkyl acrylamide polymers and include homopolymers and copolymers prepared from monomers of the acrylamide family, such as acrylamide, methacrylamide and hydroxypropylacrylamide. In the studies performed in support of the invention, a copolymer based on N-(2-hydroxypropyl)-methacrylamide (HPMA) was prepared by copolymerizing HPMA with a monomer unit having an oligopeptide side chain for attachment of a platinum compound. The copolymer was reacted with a platinum compound to form a polymer-platinum compound having anti-tumor activity in a tumor-bearing mammal.

1. Preparation of Exemplary HPMA Copolymer

An exemplary polymer prepared in support of the invention is a copolymer composed of two repeat units. One is a repeat unit of N-alkyl acrylamide. The other unit is designed to carry an oligopeptide side chain which terminates in an end group for attachment with a platinum compound. The exemplary N-alkyl acrylamide copolymer has the general structure:

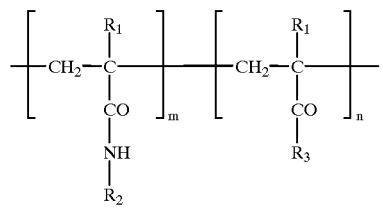

where $R_1$ is H or $CH_3$, $R_2$ is a lower alkyl or lower hydroxyalkyl group, and $R_3$ is an alkyl chain or a peptidyl side chain, described below, and m and n are each between 0.1–99.9 mole percent, more preferably between 1–99 mole percent, most preferably between 5–95 mole percent.

"Alkyl" refers to hydrocarbon chains, typically ranging about 1 to 12 carbon atoms in length. The hydrocarbon chains may be saturated or unsaturated and may optionally contain additional functional groups attached thereto, such as hydroxyl or halo. The hydrocarbon chains may be branched or straight chain. Exemplary alkyl groups include ethyl, propyl, 1-methylbutyl, 1-ethylpropyl and 3-methylpentyl.

"Lower alkyl" refers to an alkyl group containing from 1 to 5 carbon atoms, and may be straight chain or branched, as exemplified by methyl, ethyl, n-butyl, i-butyl, t-butyl, including fluorinated, monohydroxy, or chlorinated forms thereof.

The oligopeptide side chain, $R_3$, is preferably composed of peptidyl or amino acid moieties which contain, or may be functionalized to contain, a functional group for binding to platinum. The side chain should not adversely affect the in vivo solubility or toxicity properties of the resultant platinum-polymer complex. In a preferred embodiment, the oligopeptide side chain terminates in a proximal end group capable of binding to a platinum compound, where binding is meant to include attaching, complexing, coordinating, chelating and covalently linking. It is also possible that the platinum compound contains or is functionalized to contain a group for reaction and complexing with the oligopeptide side chain.

"Amino acid" refers to any compound containing both an amino group and a carboxylic acid group. The amino group may occur at the position adjacent to the carboxy function, such as in the α-amino acids, or at any location within the molecule. The amino acid may also contain additional functional groups, such as amino, thio, carboxyl, carboxamide, imidazole, etc. The amino acid may be synthetic or naturally occurring.

"Oligopeptide" or "peptidyl" refer to two or more amino acids joined together. Representative oligopeptides include, but are not limited to, amino acid combinations of Gly-Gly (SEQ ID NO:1), Gly-Phe-Gly (SEQ ID NO: 2), Gly-Phe-Phe (SEQ ID NO: 3), Gly-Leu-Gly (SEQ ID NO: 4), Gly-Val-Ala (SEQ ID NO: 5), Gly-Phe-Ala (SEQ ID NO: 6), Gly-Leu-Phe (SEQ ID NO: 7), Gly-Leu-Ala(SEQ ID NO: 8), Ala-Val-Ala (SEQ ID NO: 9), Gly-Phe-Leu-Gly (SEQ ID NO: 10), Gly-Phe-Phe-Leu (SEQ ID NO: 11), Gly-Leu-Leu-Gly (SEQ ID NO: 12), Gly-Phe-Tyr-Ala (SEQ ID NO: 13), Gly-Phe-Gly-Phe (SEQ ID NO: 14), Ala-Gly-Val-Phe (SEQ ID NO: 15), Gly-Phe-Phe-Gly (SEQ ID NO: 16), Gly-Phe-Leu-Gly-Phe (SEQ ID NO: 17), Gly-Gly-Phe-Leu-Gly-Phe (SEQ ID NO: 18). Preferred oligopeptides are of the form Gly-(W)$_p$-Gly, where p is 0–3 and (W) is any amino acid or combination of any amino acids. Two examples include Gly-Gly (SEQ ID NO:1) and Gly-Phe-Leu-Gly (SEQ ID NO:10). The platinum compound can be complexed to the amide or carboxyl groups of the oligopeptide, or, as will be discussed below, the peptidyl side chains terminate in a proximal end group for complexing with the platinum in either mono-dentate or bi-dentate binding.

As mentioned above, in a preferred embodiment, the oligopeptide side chain covalently carries on its proximal end a group through which the platinum compound is complexed to the polymer. The end group in general is one having moieties suitable for binding platinum via bonds that are preferably stable in vitro, but can be cleaved in vivo to release the active form of the platinum compound. Exemplary end groups include hydroxy, carboxy, a variety of α,ω-amines including ethylenediamine and ethylenetriamine, and complex or chelate rings such as a malonyl moiety.

A preferred copolymer for use in the compound of the present invention is a copolymer of HPMA. With reference to the structure above, an HPMA copolymer is where $R_1$ is $CH_3$ and $R_2$ is $CH_2CHOHCH_3$ (hydroxypropyl). Studies were performed in support of the present invention by preparing HPMA copolymers including either Gly-Gly (SEQ ID NO:1) or Gly-Phe-Leu-Gly (SEQ ID NO:10) oligopeptide side chains with proximal end groups of ethylenediamine, carboxyl or malonate, as will be described.

Figure 1B:
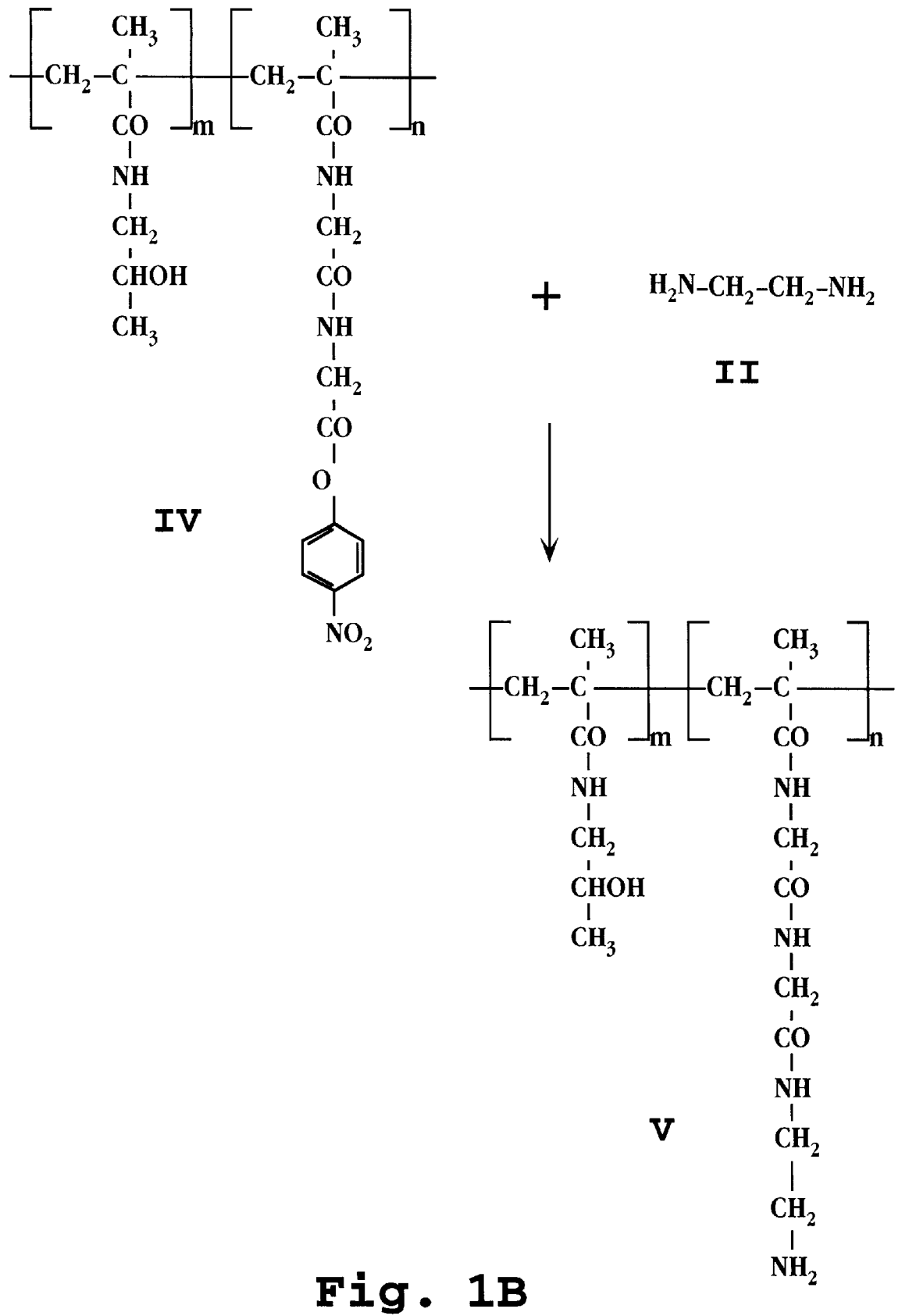

FIGS. 1A–1B show reaction schemes for synthesis of a hydroxypropyl methylacrylamide (HPMA) copolymer carrying a peptidyl side chain of Gly-Phe-Leu-Gly (SEQ ID NO:10) (FIG. 1A) or Gly-Gly (SEQ ID NO:1) (FIG. 1B) and a proximal end group of ethylenediamine. As described in Example 1, the HPMA-Gly-Phe-Leu-Gly-ethylenediamine copolymer (SEQ ID NO:10) (Compound III in FIG. 1A) is prepared by reacting an HPMA copolymer containing a Gly-Phe-Leu-Gly-p-nitrophenol (SEQ ID NO:10) (Compound I) side chain with ethylenediamine (Compound II). Preparation of the HPMA copolymers containing peptidyl-p-nitrophenol has been described by Duncan (Duncan, et al., 1987), which, in its entirety, is herein incorporated by reference.

Figure 2:
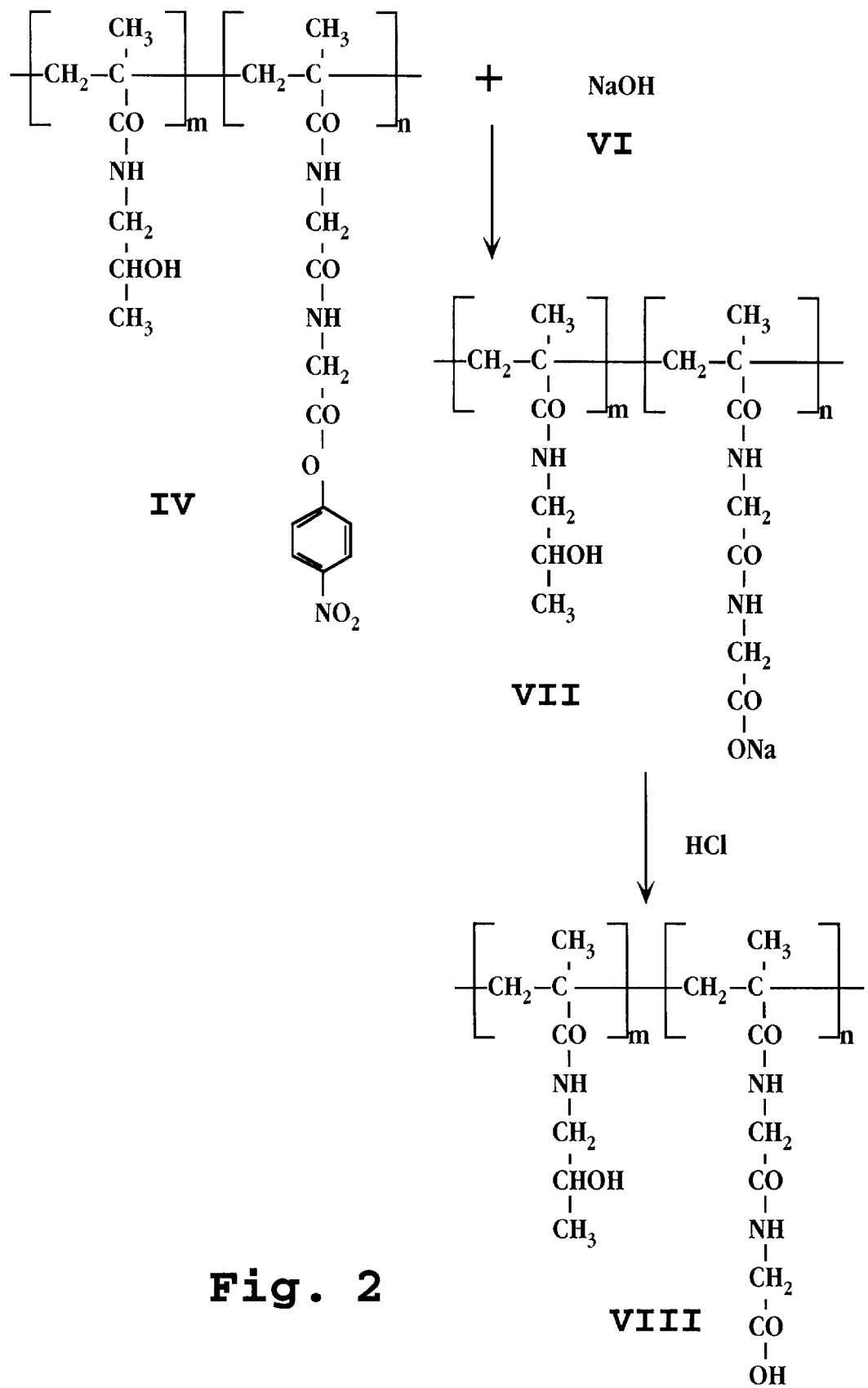
FIG. 2 is a reaction scheme for synthesis of a HPMA copolymer carrying a Gly-Gly (SEQ ID NO:1) oligopeptide side chain having a carboxyl end group.

FIG. 2 shows a reaction scheme for synthesis of an HPMA copolymer carrying peptidyl-carboxy pendant groups, where the peptidyl side chain is Gly-Gly (SEQ ID NO:1). As described in Example 2, an HPMA copolymer containing a Gly-Gly-p-nitrophenol side chain (Compound IV) is prepared and treated with sodium hydroxide (Compound VI) to form the sodium carboxylate (Compound VII). Reaction with 0.02 M HCl produces the desired HPMA copolymer carrying a Gly-Gly oligopeptide side chain with a carboxyl end group (Compound VIII).

Figure 5A:
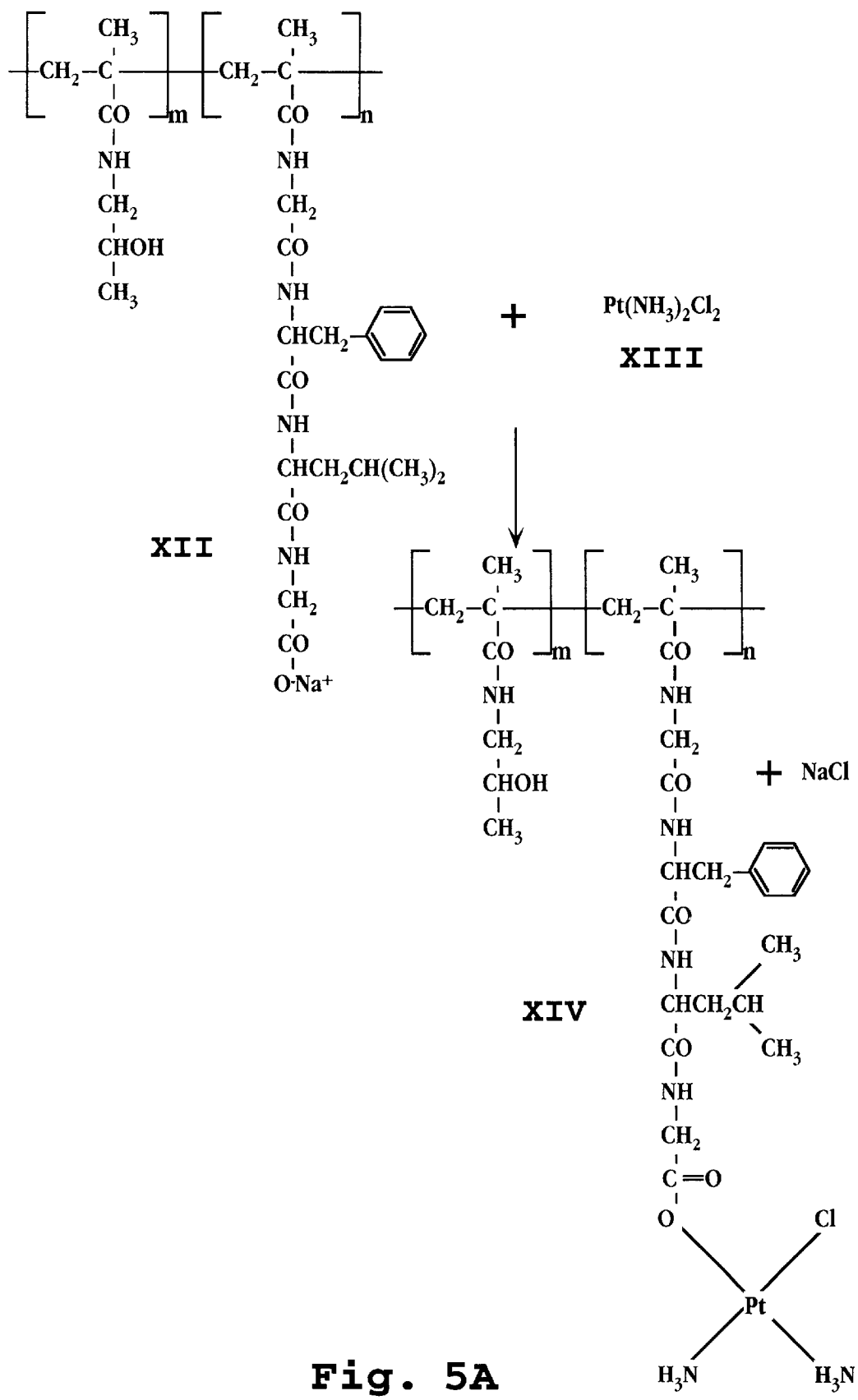
FIGS. 5A–5B are reaction schemes for synthesis of polymer-platinum compounds, where the polymer is an HPMA copolymer having a Gly-Phe-Leu-Gly (SEQ ID NO:10) (FIG. 5A) or Gly-Gly (SEQ ID NO:1) (FIG. 5B) oligopeptide side chain terminating in a carboxyl group.

The reaction scheme of FIG. 2 is also suitable for synthesis of an HPMA copolymer containing a Gly-Phe-Leu-Gly (SEQ ID NO:10) oligopeptide side chain with a terminal carboxyl group (Compound XII, FIG. 5A).

As discussed above, the polymer for use in the polymer-platinum complex is, in another embodiment, a homopolymer, in particular a homopolymer prepared from monomers of the acrylamide family. The homopolymer is derivatized with a side chain for attachment of the platinum compound, according to methods known to those of skill in the art.

The synthetic polymer for use in the polymer-platinum complex of the present invention has a molecular weight of between about 1,000–5,000,000 daltons, more preferably between 5,000–1,000,000 daltons. The molecular weight is an important parameter in determining the blood circulation lifetime and body distribution of the compound, in particular its enhanced endothelial permeation and retention at the tumor. The polydispersity of the polymer is also a factor in circulation lifetime and distribution (Seymour, et al., 1987).

As discussed above, the polymer for use in the polymer-platinum compound is one which is soluble in a physiologically acceptable medium. Preferably, the polymer is water soluble, for administration in saline or other aqueous-based pharmaceutical carriers.

The polymers prepared as described in Examples 1 and 2 were tested for biocompatibility, as described in Example 3. The cytotoxicity of the polymers was determined by adding the HPMA copolymers to cultures of L132 (human embryonic lung cells) or B16 melanoma cells and incubating for 72 hours. After incubation, 5-dimethylthiazol-2-yl-2,5-diphenyl tetrazolium bromide (MTT) was added to the culture medium and incubated before removal of the culture medium and addition of dimethylsulfoxide to dissolve the MTT crystals. The absorbance of the cells was quantified to measure the viability of the test cultures relative to a control culture of cells in the absence of polymer. A positive control of poly-L-lysine was also tested. No toxicity of the HPMA copolymers was observed in comparison to dextran as a negative control and poly-L-lysine, as a positive control.

Figure 3:
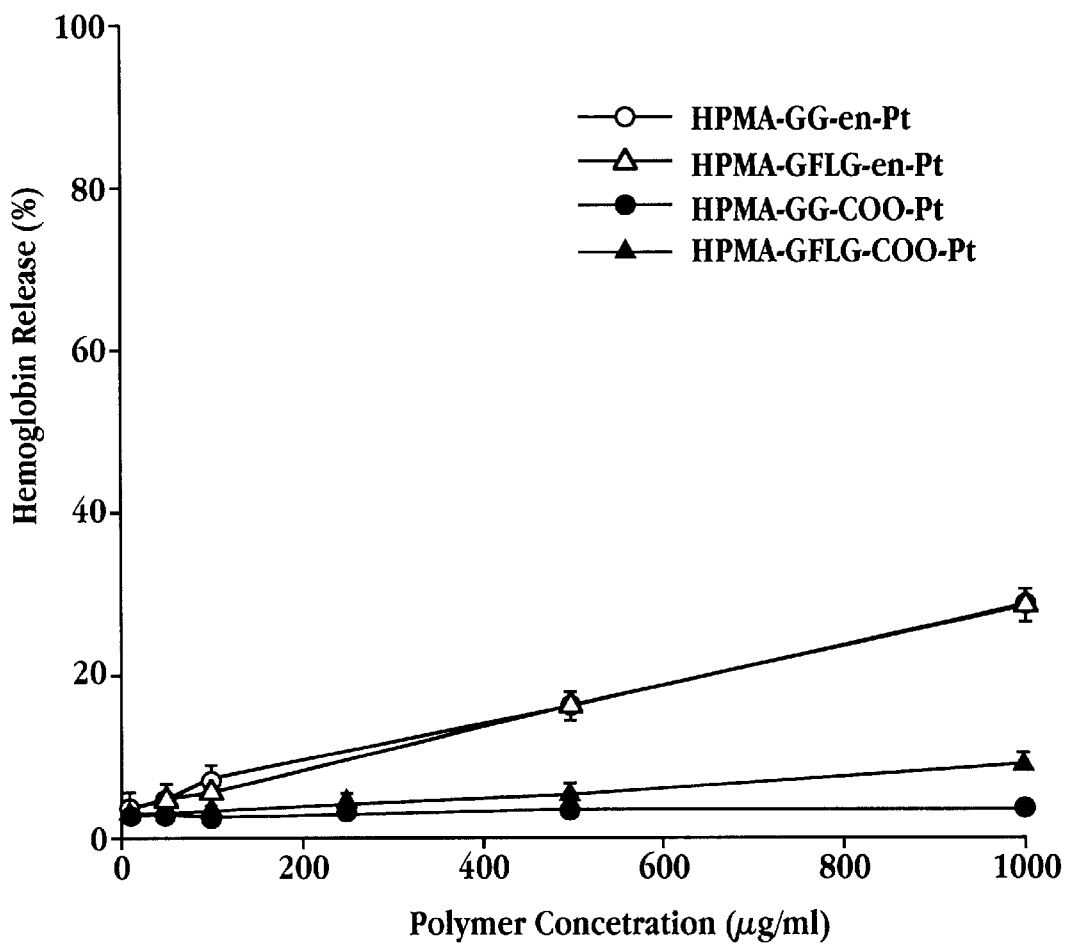
FIG. 3 is a plot of red blood cell lysis, expressed as a percentage of a control detergent causing complete lysis, as a function of polymer concentration in $\mu$g/ml, for HPMA-Gly-Gly-ethylenediamine open circles), HPMA-Gly-Phe-Leu-Gly-ethylenediamine (SEQ ID NO:10) (open triangles), HPMA-Gly-Gly-COOH (closed circles) and HPMA-Gly-Phe-Leu-Gly-COOH (SEQ ID NO:10) (closed triangles)

Biocompatibility of the HPMA copolymers was also determined by evaluation of the ability of the polymers to lyse red blood cells. As described in Example 3B, red blood cells suspended in phosphate buffered saline were added to the HPMA copolymers and incubated for 1 hour or for 24 hours. Poly-L-lysine was used as a positive control polymer and the detergent Triton X100 was used to produce 100% lysis. After incubation, the test cells were centrifuged and the supernatants analyzed for hemoglobin release. The results are shown in FIG. 3 where red blood cell lysis, expressed as a percentage of a control detergent causing complete lysis, is shown as a function of polymer concentration in μg/ml, for HPMA-Gly-Gly-ethylenediamine (open circles), HPMA-Gly-Phe-Leu-Gly-ethylenediamine (SEQ ID NO:10) (open triangles), HPMA-Gly-Gly-COOH (closed circles) and HPMA-Gly-Phe-Leu-Gly-COOH (SEQ ID NO:10) (closed triangles). The data shows that the HPMA copolymers do not significantly lyse red blood cells.

2. Preparation of Polymer-Platinum Compounds

The HPMA copolymers prepared as described in Examples 1 and 2 were used to prepare polymer-platinum compounds in accordance with the invention.

Figure 4A:
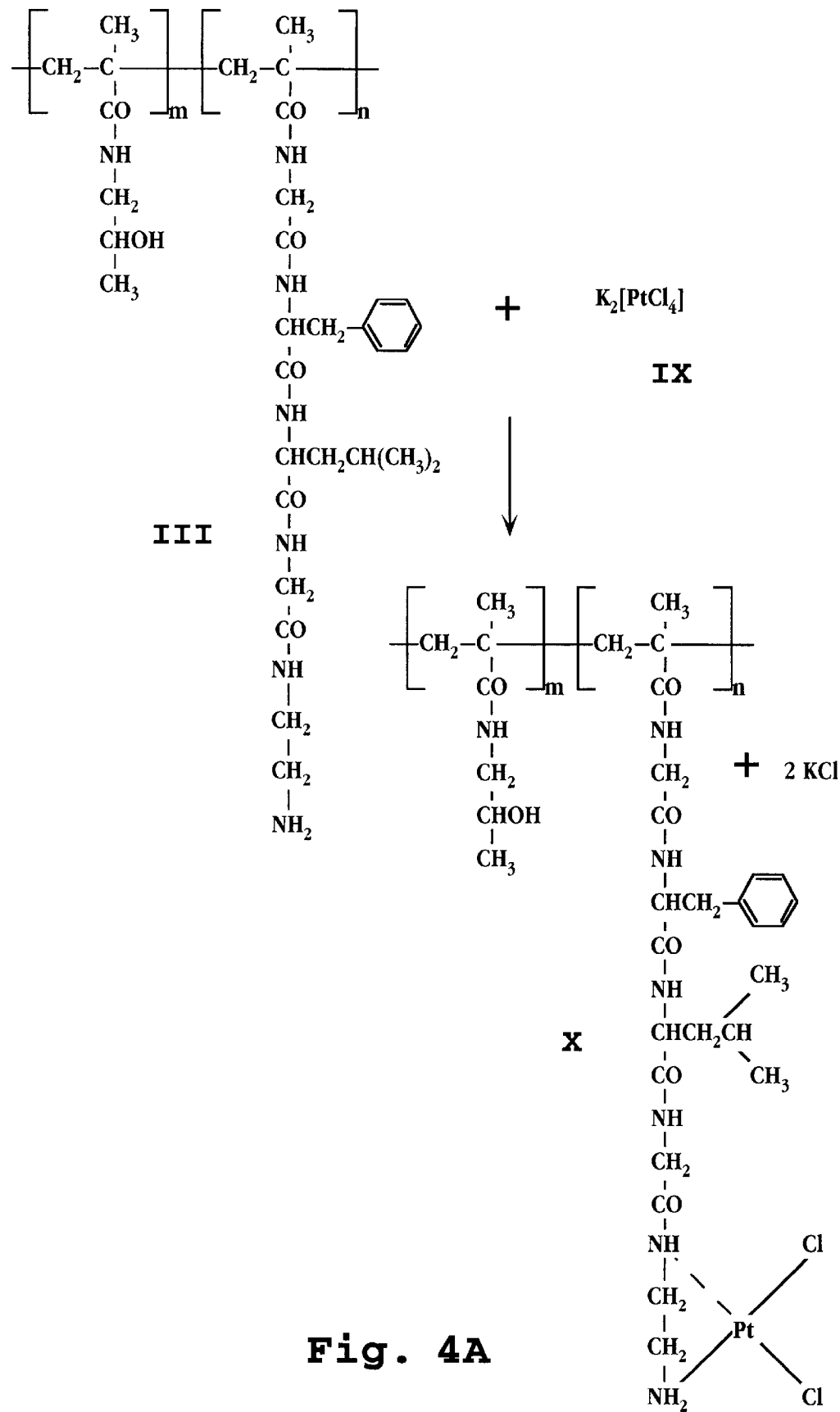
FIGS. 4A–4B are reaction schemes for synthesis of polymer-platinum compounds, where the polymer is an HPMA copolymer having a Gly-Phe-Leu-Gly (SEQ ID NO:10) oligopeptide side chain with an ethylenediamine end group (FIG. 4A) and a Gly-Gly (SEQ ID NO:1) oligopeptide side chain with a terminal ethylenediamine group (FIG. 4B)

FIG. 4A shows a reaction scheme for synthesis of a polymer-platinum compound composed of an HPMA copolymer having a Gly-Phe-Leu-Gly (SEQ ID NO:10) oligopeptide side chain terminated with ethylenediamine. As described in Example 4A, the HPMA copolymer is reacted with potassium tetrachloro platinate(II) (Compound IX) to form a compound with platinum bound to the amine functionalities in the ethylenediamine end group (Compound X).

Figure 4B:
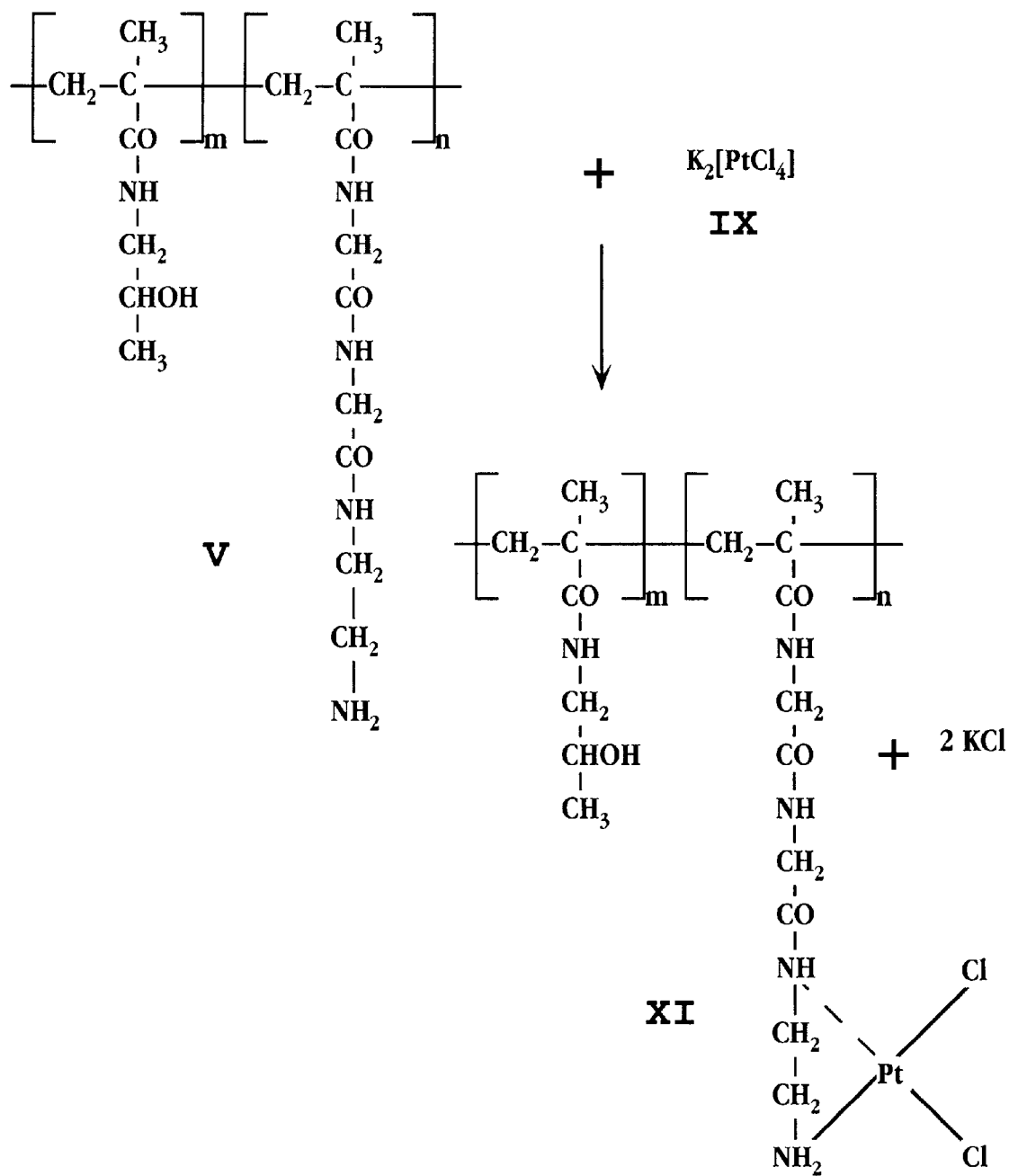

FIG. 4B is a similar reaction scheme for an HPMA copolymer having a Gly-Gly (SEQ ID NO:1) side chain terminated with ethylenediamine, prepared as described with respect to FIG. 1B. As detailed in Example 4B, reaction with potassium tetrochloroplatinate results in a compound with the platinum bound to the amine groups in the ethylenediamine terminal end group (Compound XI).

Solubility studies of the polymer-platinum compounds shown in FIGS. 4A–4B were performed to determine solubility in water at 25° C. The results, shown in Table 1 and compared to the water solubility of cisplatin, show that the polymer-platinum compounds have a water solubility of greater than about 320 mg/ml, a significant improvement over the solubility of cisplatin. Stability data on the compounds shown in Table 1 indicate that the compounds remain in solution, e.g. are stable, for greater than 6 months.

TABLE 1

| Compound or Drug | Pt[1] Content (wt %) | Water Solubility mg/ml |
|---|---|---|
| HPMA-GFLG-en[2]-Pt (SEQ ID NO:10) | 6.5 | >323 |
| HPMA-GG-en[2]-Pt | 4.6 | >345 |
| cisplatin | — | 2 |

Figure 5B:
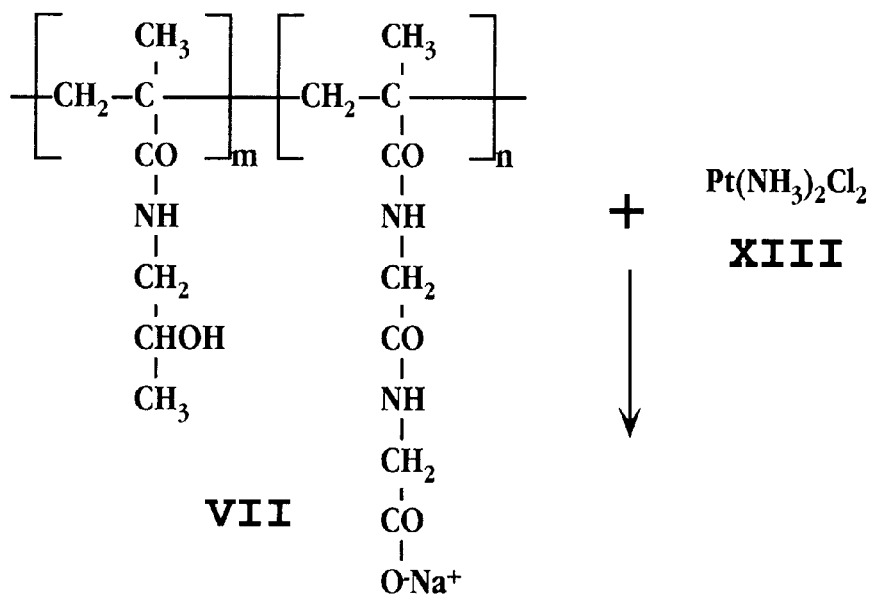
Figure 5B:
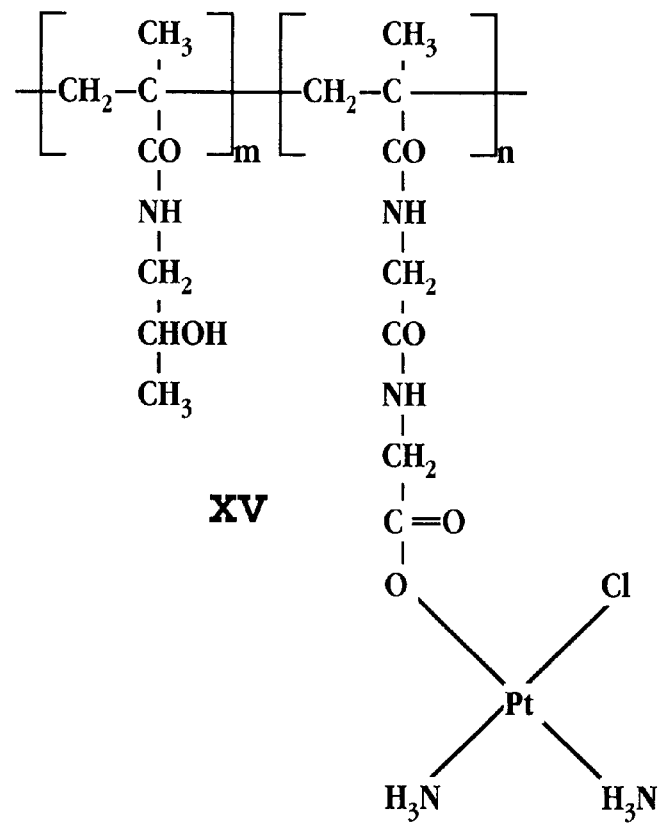

[1]Wt % Pt determined by atomic absorption spectroscopy.
[2]en = ethylenediamine Synthesis of polymer-platinum compounds from HPMA copolymers having a peptidyl side chain with a terminal, free acid hydroxyl group is shown in FIGS. 5A–5B and described in Example 5. In FIG. 5A, HPMA copolymer having a Gly-Phe-Leu-Gly (SEQ ID NO:10) side chain and a terminal carboxyl group is reacted with cisplatin (Compound XIII), yielding a polymer-platinum compound where platinum is complexed to the polymer via the carboxyl group (Compound XIV). FIG. 5B shows a similar reaction for an HPMA copolymer having a Gly-Gly (SEQ ID NO:1) side chain.

Figure 6:
FIG. 6 is a reaction scheme for synthesis of a polymer-platinum compound according to another embodiment of the invention, where the polymer is an HPMA copolymer having a Gly-Phe-Leu-Gly (SEQ ID NO:1) peptide side chain terminating in a malonyl moiety for attachment with the platinum compound.
Figure 6:
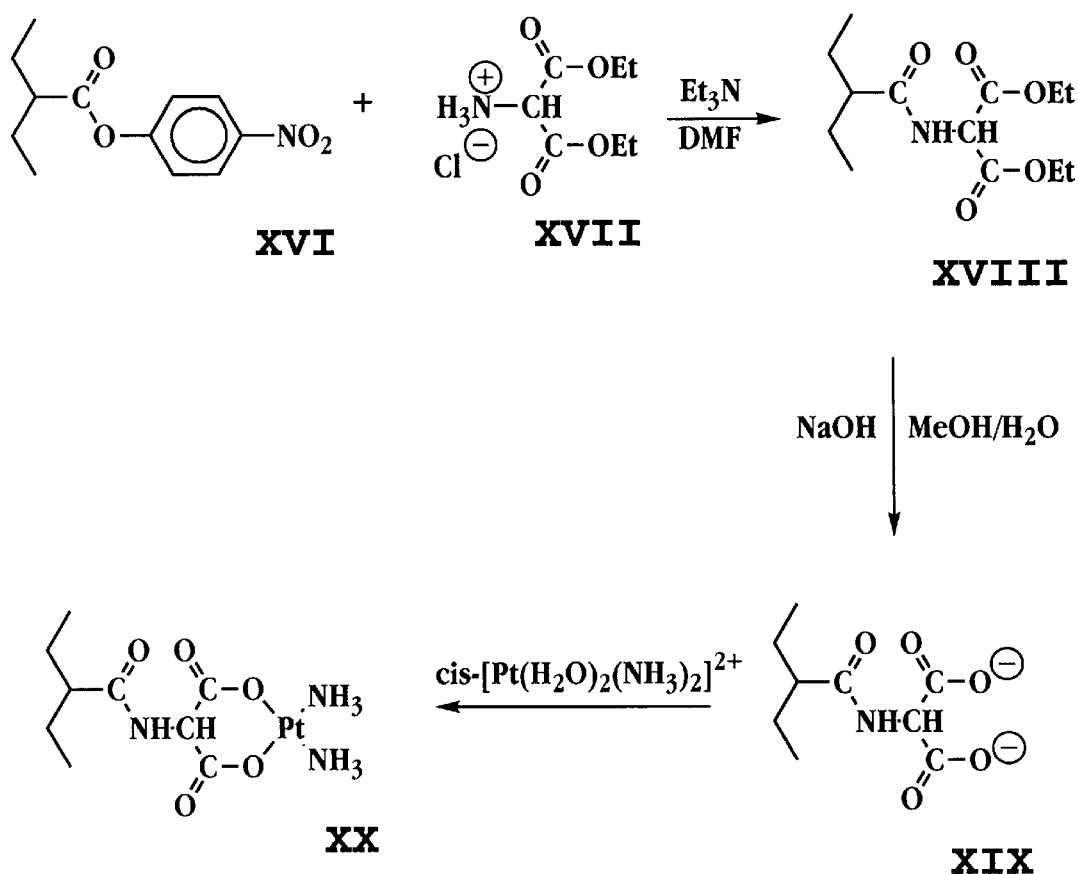
Figure 7A:
FIGS. 7A–7E show polymer-platinum compounds according to other embodiments of the invention.
Figure 7A:
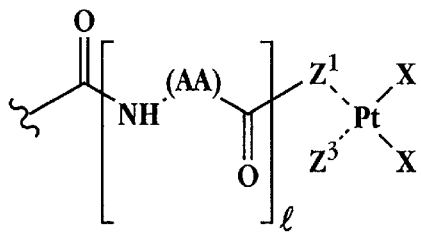
Figure 7B:
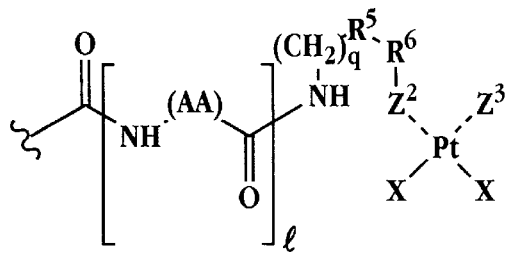
Figure 7C:
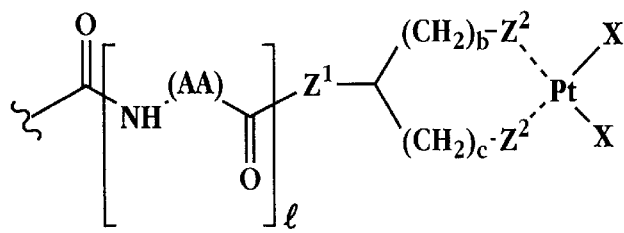
Figure 7D:
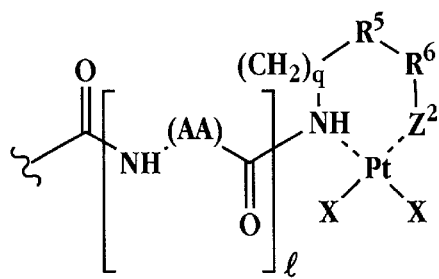
Figure 7E:
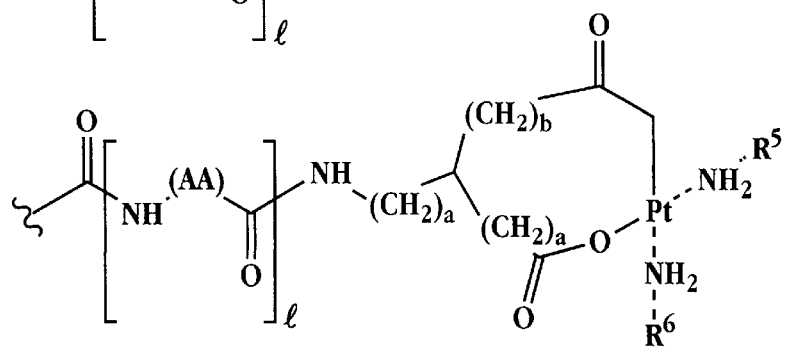

FIG. 6 is a reaction scheme for synthesis of a polymer-platinum compound according to another embodiment of the invention, where the polymer is an HPMA copolymer having a Gly-Phe-Leu-Gly (SEQ ID NO: 10) peptide side chain terminating in a malonyl moiety for attachment with the platinum compound. The polymer is prepared by reacting the HPMA copolymer with the Gly-Phe-Leu-Gly-p-nitrophenol (SEQ ID NO:10) side chain (Compound XVI) with diethylaminomalonate hydrochloride (Compound XVII). The product (Compound XVIII) is treated as described in Example 6 and finally reacted with cis-[Pt(NH$_3$)$_2$(H2O)$_2$]$^{2+}$ (prepared as described in Example 6A) to yield the desired polymer-platinum compound (Compound XX).

The polymer-platinum compounds described above were prepared using cisplatin or potassium tetrochloroplatinate as the starting material for platinum. It will be appreciated that any of a number of readily available or synthesized platinum complexes can be utilized to form the polymer-platinum complex of the present invention. The platinum starting material should possess at least one readily displacable ligand, preferably two, for complexing with the polymer, and is preferably water soluble, for ease of synthesis. The starting platinum compound does not necessarily have therapeutic activity in vivo, and is preferably converted in vivo to a biologically active form upon biologically-induced displacement of the polymer in whole or in part. More preferably, the platinum compound is converted in vivo at the intended target site to a biologically active form by release of the polymer in whole or in part.

It will also be appreciated that the platinum compound can be complexed to the polymer through attachment to the amides or carboxyl groups of the peptidyl side chains. In the embodiments where the side chains include a proximal end group for attaching the platinum compound, it will be appreciated that the compound can be attached in such a way to yield either a mono-dentate species, a bi-dentate species, or a mixture thereof. The reactions conditions set forth above for preparation of the polymer-platinum compound yield a mixture of mono-dentate and bi-dentate species. The reaction conditions can be selected accordingly to favor one or more of these species. It will also be appreciated that other end groups for attaching the platinum compound are contemplated, and some examples are shown in FIG. 7. In these structures, the polymer backbone is represented by a wavy line and a single peptidyl side chain is shown attached to the polymer, and (AA) is any amino acid; l is 0–4; q is 0–2; $Z^1$ is O or NH; $Z^2$ is OH or NH$_2$; $Z^3$ is OH$_2$, NH$_3$, NH$_2$R$_4$ where R$^4$ is a lower alkyl; X is F, Br, Cl, I, OH or water; a is 0–9; b and c can independently be 0–2 but together do not sum greater than 2; $R^5$ and $R^6$ are H, lower alkyl or taken together form a ring of 5–7 atoms.

II. In vitro Characterization of the Polymer-Platinum Compounds

As described in Example 7A–7C, the polymer-platinum compounds prepared as described above (Examples 4, 5 and 6) were tested in vitro for release of platinum. The in vitro release was determined at pH 5.5 and at pH 7.4 by dissolving the test compounds in citrate phosphate buffer or in phosphate buffered saline (PBS), respectively. The free Pt in the buffer was analyzed using the o-PDA assay or by AAS as described in the Methods section below.

Figure 8A:
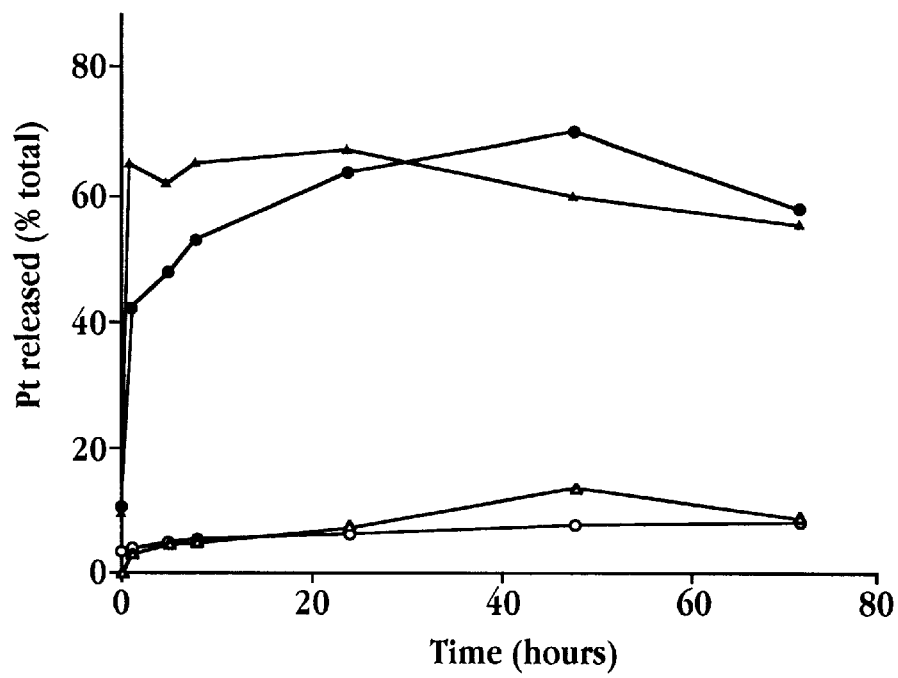
FIGS. 8A–8B are plots showing the percentage of platinum released in vitro from HPMA copolymer-platinum compounds as a function of time, in hours, at pH=5.5 (FIG. 8A) and pH=7.4 (FIG. 8B) for HPMA-Gly-Gly-ethylenediamine-Pt (open circles), HPMA-Gly-Phe-Leu-Gly-ethylenediamine-Pt (SEQ ID NO:10) (open triangles), HPMA-Gly-Gly-O-Pt (closed circles) and HPMA-Gly-Phe-Leu-Gly-O-Pt (SEQ ID NO:10) (closed triangles)
Figure 8B:
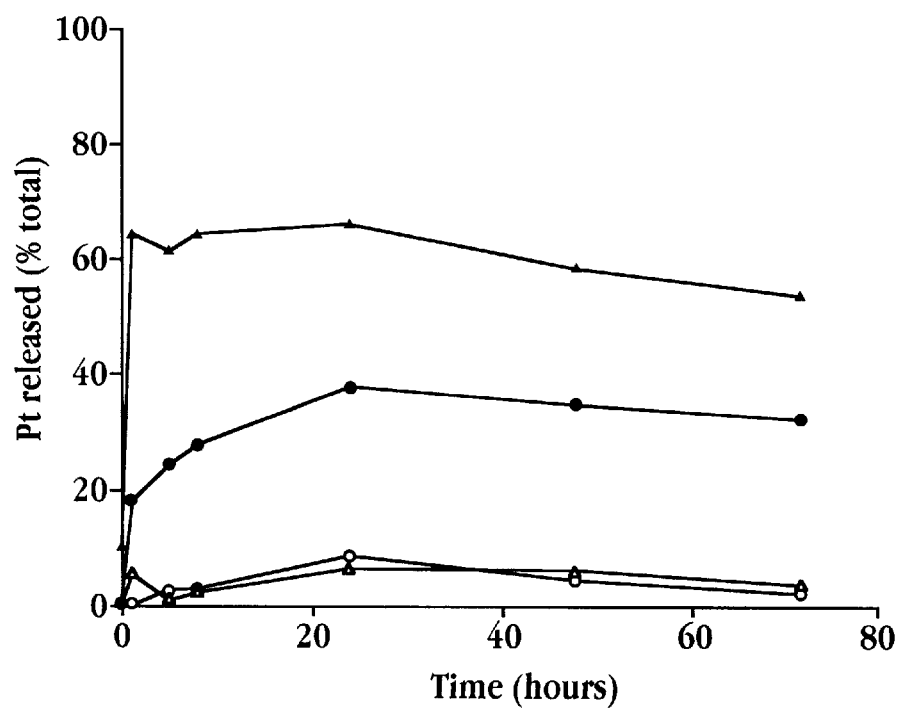

The results for polymer-platinum compounds having ethylenediamine and carboxyl proximal end groups are shown in FIGS. 8A–8B, where the concentration of Pt released from the polymer-platinum compounds, expressed as a percentage of the total available, is plotted as a function of time. As seen, at pH 5.5 (FIG. 8A) and at pH 7.4 (FIG. 8B) the HPMA copolymers having a side chain with a terminal carboxyl group, HPMA-Gly-Gly-O-Pt (closed circles) and HPMA-Gly-Phe-Leu-Gly-O-Pt (SEQ ID NO:10) (closed triangles) release the platinum more quickly than the ethylenediamine terminated copolymers, HPMA-Gly-Gly-ethylenediamine-Pt (open circles) and HPMA-Gly-Phe-Leu-Gly-ethylenediamine-Pt (SEQ ID NO:10) (open triangles).

These results indicate that platinum attached to the polymer through a carboxyl end group is released more rapidly than platinum attached to the polymer through an ethylenediamine end group. The results also suggest that the peptidyl side chains terminating in the ethylenediamine species must first be enzymatically cleaved to release a platinum species.

As can be seen, the HPMA Gly-Gly-O-Pt and HPMA-Gly-Phe-Leu-Gly-O-Pt (SEQ ID NO:10) release platinum at approximately equivalent rates at pH 5.5. At pH 7.4, the polymer having the shorter Gly-Gly (SEQ ID NO:1) side chain releases Pt at approximately 50% the rate at pH 5.5. This result indicates that the rate of release of the platinum compound from the polymer-platinum compound can be controlled through selection of the composition and length of the side chain.

Figure 9A:
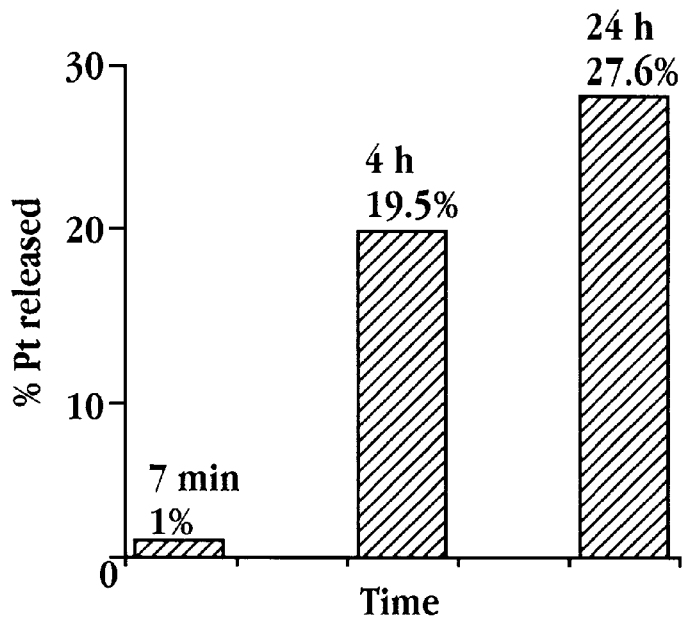
FIGS. 9A–9B are plots showing in vitro release of platinum from the polymer-platinum compound HPMA-Gly-Phe-Leu-Gly-malonate-Pt (SEQ ID NO:10) into saline as a function of time, where the platinum released is measured by AAS (FIG. 9A) and by o-phenylenediamine colorimetric assay (FIG. 9B)
Figure 9B:
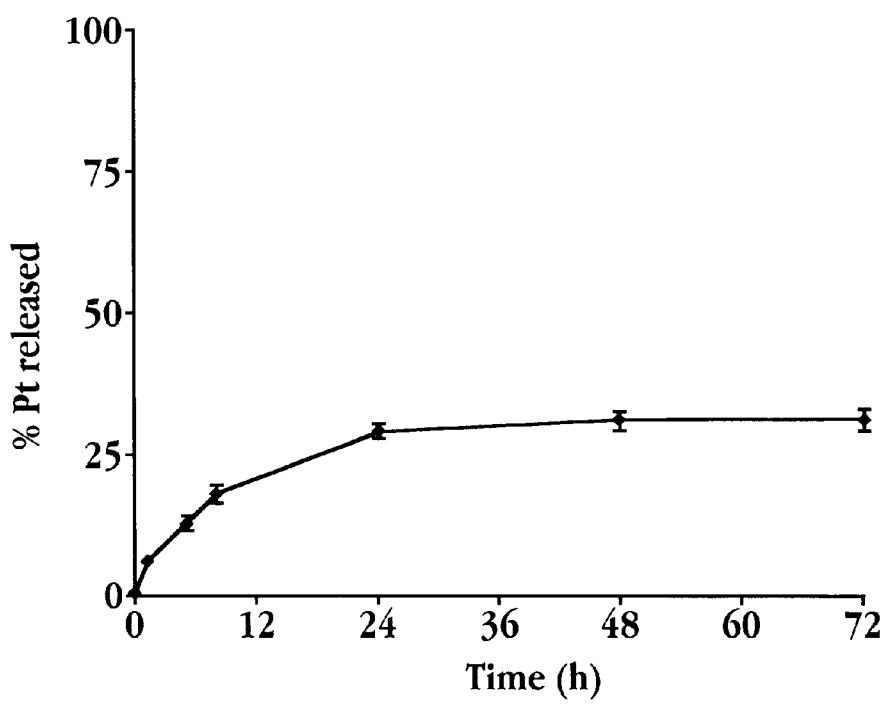

The in vitro release results for the polymer-platinum compound having a malonate end group is shown in FIGS. 9A–9B. In FIG. 9A, the compound (prepared as described in Example 6) was dissolved in phosphate buffered saline, pH 7.4 at 37° C. and the solution was sampled at 7 minutes, 4 hours, and 24 hours, as described more fully in Example 7B. The samples were analyzed for Pt content by AAS and the results are shown as a percentage of the total. In FIG. 9B, the platinum release from the same polymer was determined as described in Example 7C, with the samples taken over a 72 hour period and analyzed for free Pt using the o-Phenylenediamine colorimetric assay. The results of FIGS. 9A and 9B are in good agreement.

In summary, the in vitro release data demonstrate that the release rate of platinum from the polymer-platinum compounds can be controlled through selection of the end group for attachment of the platinum, through the composition and length of the oligopeptide side chain and by pH.

III. In vivo Characterization of Polymer-Platinum Compound

The polymer-platinum compounds prepared as described above were tested in vivo in mice to evaluate anti-tumor activity, toxicity and biodistribution. The antitumor activity and toxicity were evaluated using the tumor models described in Example 8.

1. L1210 Tumor Inoculated Intraperitoneally

As described in Example 8A, the polymer-platinum compounds were tested against an L1210 intraperitoneal (i.p.) tumor model. The tumor was inoculated on day 0 and followed by treatment on days 1, 2 and 3 with HPMA-Gly-Phe-Leu-Gly-ethylenediamine-Pt (SEQ ID NO:10) or HPMA-Gly-Gly-ethylenediamine-Pt, administered intraperitoneally at various dosages, administered as a single dose per 24 hour period. Free cisplatin was administered as a comparative treatment. The results are shown in Table 2.

TABLE 2

| Treatment | Dose Pt (mg/kg)[1] | T/C[2] | Toxic Deaths |
|---|---|---|---|
| Cisplatin | 2 | 171 | 0/10 |
| | 3 | 64 | 9/10 |
| HPMA-GFLG-en[3]-Pt | 3 | 150 | 0/5 |
| (SEQ ID NO:10) | 5 | 137 | 0/5 |
| | 10 | 126 | 0/5 |
| | 15 | 131 | 0/10 |
| | 30 | 70 | 2/5 |
| | 45 | 30 | 5/5 |
| HPMA-GG-en[3]-Pt | 6 | 114 | 0/5 |
| | 19 | 38 | 5/5 |
| | 38 | 20 | 5/5 |
| | 57 | 20 | 5/5 |

[1]the indicated dose was administered once a day for 3 days following tumor inoculation.
[2]T/C = ratio of the mean survival time of treated animals divided by the mean survival of the untreated control group × 100.
[3]en = ethylenediamine As seen in Table 2, the maximum tolerated dose of free cisplatin in this model was 2 mg/kg administered once a day for three days. The HPMA copolymer having the enzymatically degradable side chain Gly-Phe-Leu-Gly (SEQ ID NO:10) terminated with an ethylenediamine end group for attachment of platinum was equally active when compared to the optimum dose of free cisplatin. However, the HPMA copolymer was significantly less toxic than free cisplatin, as evidenced by the more than seven-fold increase in platinum dosage, e.g., 15 mg/kg once per day for three days compared to 2 mg/kg for free cisplatin, administered with no toxic deaths. It is also noted that the HPMA-Gly-Phe-Leu-Gly-ethylenediamine-Pt compound (SEQ ID NO:10) had anti-tumor activity at a dose of 3 mg/kg per day for three days. In contrast, free cisplatin was toxic at this dosage.

With continuing reference to Table 2, the HPMA copolymer having the non-enzymatically biodegradable side chain Gly-Gly (SEQ ID NO:1) with a terminal ethylenediamine group for attachment of platinum did not show significant activity over the dosage range tested.

2. Intraperitoneal B16 Melanoma Tumor Model

As described in Example 8B, the polymer-platinum compound HPMA-Gly-Phe-Leu-Gly-ethylenediamine-Pt (SEQ ID NO:10) was tested against a B16 melanoma model inoculated intraperitoneally (i.p.). On the day after inoculation, the HPMA copolymer was administered i.p. as a single dose at platinum concentrations of 5, 10, 15 and 20 mg/kg. The results are shown in Table 3.

TABLE 3

| Treatment | Dose Pt (mg/kg) | T/C[1] | Toxic Deaths |
|---|---|---|---|
| Cisplatin | 5 | 89 | 2/5 |
| HPMA-GFLG-en[2]-Pt | 5 | 99 | 0/5 |
| (SEQ ID NO:10) | 10 | 104 | 0/5 |
| | 15 | 105 | 0/5 |
| | 20 | 100 | 0/5 |

[1]T/C = ratio of the mean survival time of treated animals divided by the mean survival of the untreated control group × 100.
[2]en = ethylenediamine The data show that the amount of platinum that can safely be administered in the form of the polymer-platinum compound is more than four-fold higher than can be administered safely for free cisplatin; e.g., 2/5 toxic deaths at 5 mg/kg free cisplatin and 0/5 toxic deaths at 20 mg/kg polymer-platinum compound.

3. B16 Melanoma Subcutaneous Tumor Model

Figure 10A:
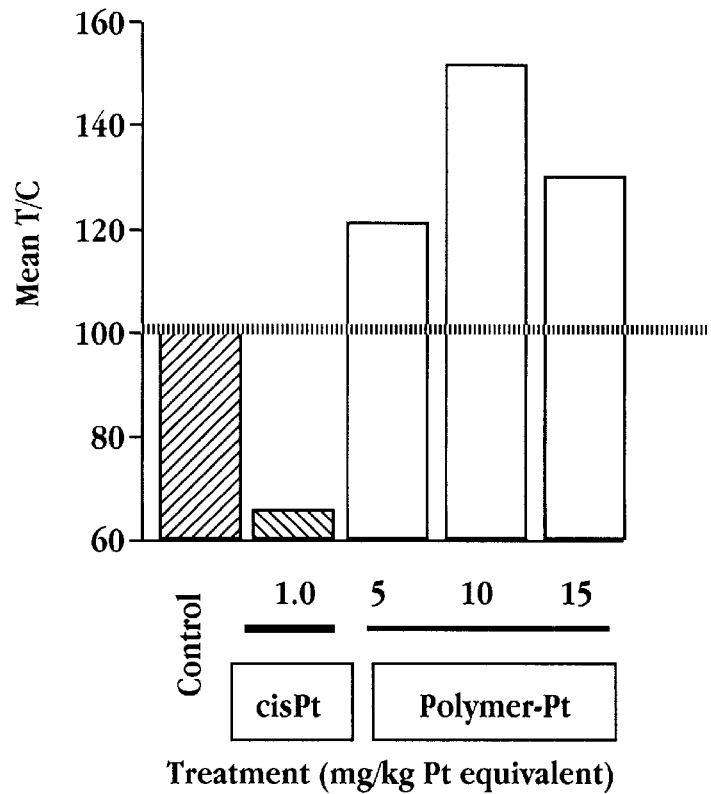
FIGS. 10A–10B are bar graphs showing the effect of HPMA-Gly-Phe-Leu-Gly-ethylenediamine-Pt (SEQ ID NO:10) (FIG. 10A) and HPMA-Gly-Phe-Leu-Gly-O-Pt (SEQ ID NO:10) (FIG. 10B) against an established B16 melanoma in mice, expressed as the ratio of the mean survival time of treated animals to the mean survival time of the untreated control animals×100 (T/C), for various dosages of platinum, and compared to animals receiving 1 mg/kg cisplatin and to untreated, control animals.
Figure 10B:
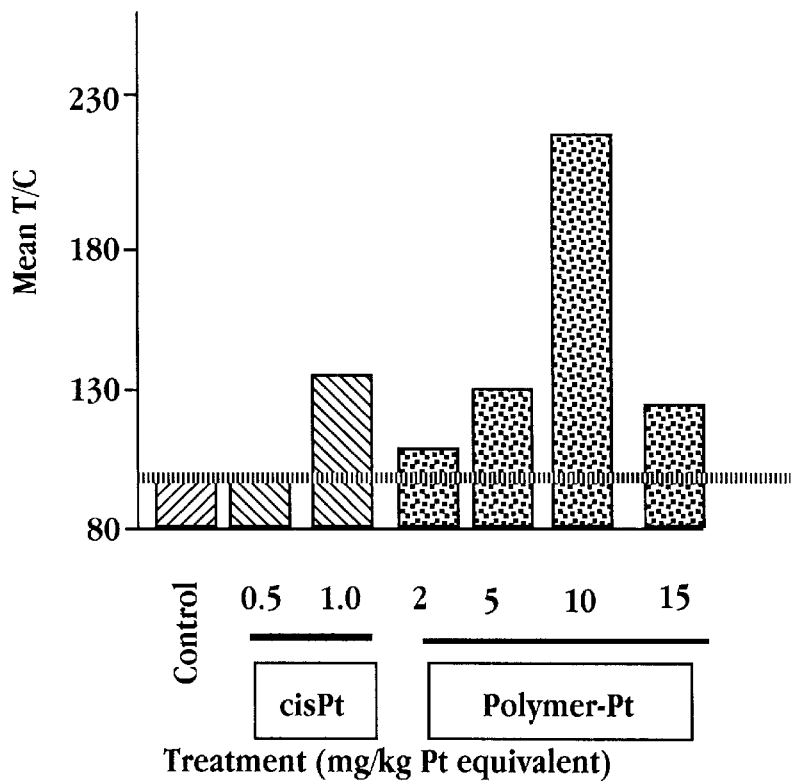

As described in Example 8C, mice were inoculated subcutaneously with B16 melanoma cells to establish a solid tumor. The activity of the HPMA copolymer platinum compounds against the tumor was tested by administering the polymer-platinum compounds HPMA-Gly-Phe-Leu-Gly-ethylenediamine-Pt (SEQ ID NO:10) and HPMA-Gly-Phe-Leu-Gly-O-Pt (SEQ ID NO:10) at platinum doses of 2, 5, 10, 15 mg/kg. The results are shown in FIGS. 10A–10B where FIG. 10A corresponds to animals treated with HPMA-Gly-Phe-Leu-Gly-ethylenediamine-Pt (SEQ ID NO:10) and FIG. 10B is for animals treated with HPMA-Gly-Phe-Leu-Gly-O-Pt (SEQ ID NO:10). The data is expressed as the ratio of the mean survival time of treated animals to the mean survival time of the untreated control animals×100 (T/C), for several platinum dosages. One animal test group received 1 mg/kg cisplatin and one group of tumor-bearing mice were left untreated as a control.

It can be seen from the data that the HPMA copolymer-platinum compound have considerably better anti-tumor activity than free cisplatin in the s.c. tumor model. With respect to the HPMA-Gly-Phe-Leu-Gly-ethylenediamine-Pt compound (SEQ ID NO:10) (FIG. 10A), anti-tumor activity was significantly improved relative to free cisplatin and was best at a platinum dosage of 10 mg/kg. The HPMA copolymer-Gly-Phe-Leu-Gly-ethylenediamine-Pt (SEQ ID NO:10) was more than 15-fold less toxic than free cisplatin.

With respect to the HPMA-Gly-Phe-Leu-Gly-O-Pt compound (SEQ ID NO:10) (FIG. 10B), anti-tumor activity was highest at 10 mg/kg, with a T/C of greater than 200. Toxic deaths at doses of 10 mg/kg and 15 mg/kg (2/6 and 4/4, respectively) occurred at the 10 kg/mg and 15 kg/mg dosages, however, the HPMA-Gly-Phe-Leu-Gly-O-Pt compound (SEQ ID NO:10) was still 5–10 fold less toxic than free cisplatin whose maximum tolerated dose in this model was 1 mg/kg.

With continuing reference to FIGS. 10A–10B, the anti-tumor activity for the compound having platinum attached through a free acid hydroxyl group, for example, as provided by a terminal carboxyl group, (FIG. 10B) showed greater anti-tumor activity than the compound with ethylenediamine-attached platinum (FIG. 10A). This result correlates with the measured rates of platinum release in vitro, discussed above (FIGS. 8A–8B). The HPMA-Gly-Phe-Leu-Gly-ethylenediamine-Pt (SEQ ID NO:10) is stable in vitro and requires enzymatic activation intratumorally for anti-tumor activity. This leads to a compound which is dramatically less toxic than the free drug. The rate of release from the enzymatically biodegradable Gly-Phe-Leu-Gly (SEQ ID NO:10) side chain can be controlled by administration of suitable enzymes to facilitate enzymatic cleavage, such as the proteases, trypsin or papain.

These results demonstrate that the rate of release of the platinum compound from the polymer-platinum compound can be controlled through selection of the end group for attachment of the platinum compound and through selection of the composition of the oligopeptide side chain.

Figure 11:
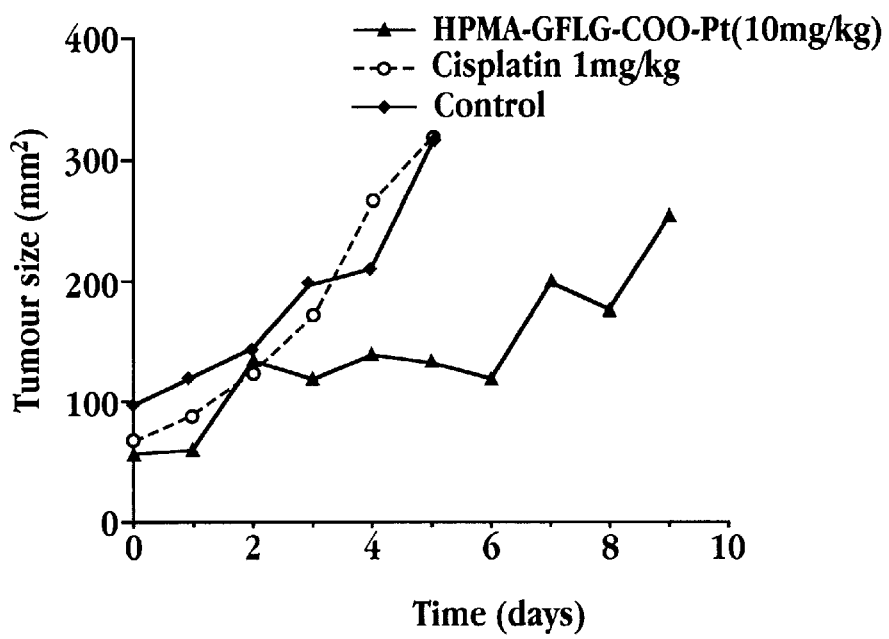
FIG. 11 is a plot showing tumor size, in $mm^2$, as a function of time, in days, for mice bearing a s.c. B16 melanoma treated with 10 mg/kg HPMA-Gly-Phe-Leu-Gly-O-Pt (SEQ ID NO:10) (closed triangles), with 1 mg/kg cisplatin (open circles) or untreated (solid line)

The tumor size of animals bearing a solid B16 tumor was monitored as a function of time, in days, for mice treated with the polymer-platinum compound HPMA-Gly-Phe-Leu-Gly-O-Pt (SEQ ID NO:10) or with cisplatin. As seen in FIG. 11, animals treated with the 10 mg/kg of the polymer-platinum complex (closed triangles) had a marked inhibition of tumor growth compared to those treated with 1 mg/kg cisplatin (open circles). The solid line represents untreated animals.

In summary, the in vivo data show that the polymer-platinum compounds of the present invention achieve an enhanced anti-tumor activity when compared to cisplatin. The polymer-platinum compounds achieve improved anti-tumor activity, at least in part, by accumulation of the compound at the tumor site. The polymer-platinum compounds are able to release a biologically active form of platinum, where the release of platinum can be controlled through selection of the end group attaching the platinum and through selection of the composition and length of the oligopeptide side chain.

Figure 12:
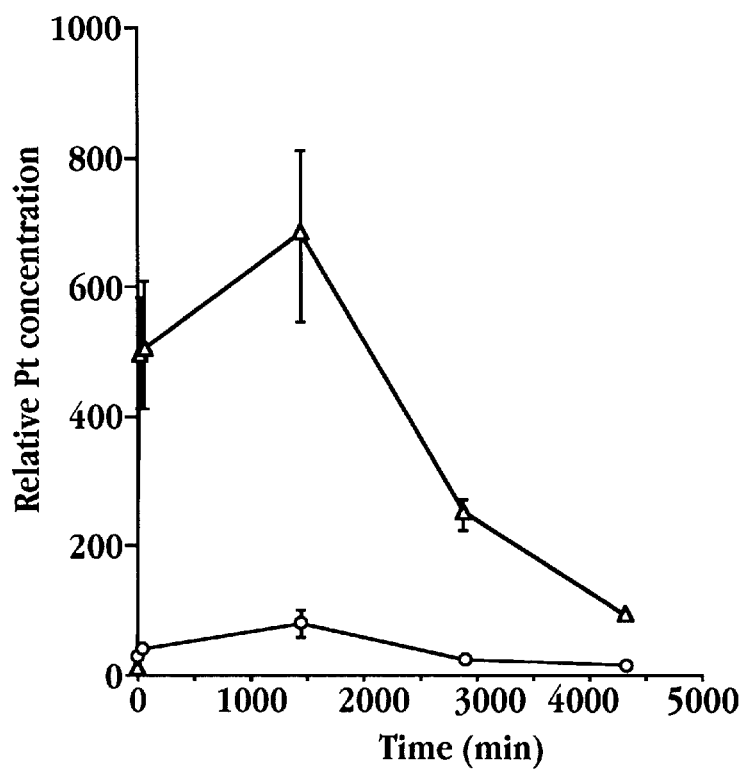
FIG. 12 is a plot showing relative platinum concentration as a function of time, in minutes, in a B16F10 tumor 72 hours after intravenous injection of 1 mg/kg HPMA-Gly-Gly-ethylenediamine-Pt (open triangles) or 1 mg/kg cisplatin (closed circles)

Further evidence of the enhanced accumulation of the polymer-platinum compound in the tumor region is shown in FIG. 12. As described in Example 9, tumor-bearing mice were treated intravenously with free cisplatin (1 mg/kg, solid circles) or HPMA-Gly-Gly-ethylenediamine-Pt (1 mg/kg, open triangle). At various times after treatment, the tumors were dissected and the platinum content determined by atomic absorption spectroscopy.

As seen in FIG. 12, the relative platinum concentration in the tumors treated with the HPMA copolymer is significantly higher than animals treated with an equivalent dose of cisplatin. This indicates that platinum administered in the form of the polymer-platinum compound achieves improved accumulation at the tumor site. This improved accumulation demonstrates an enhanced or selective directing or targeting of the polymer-platinum compounds to the tumors.

Figure 13:
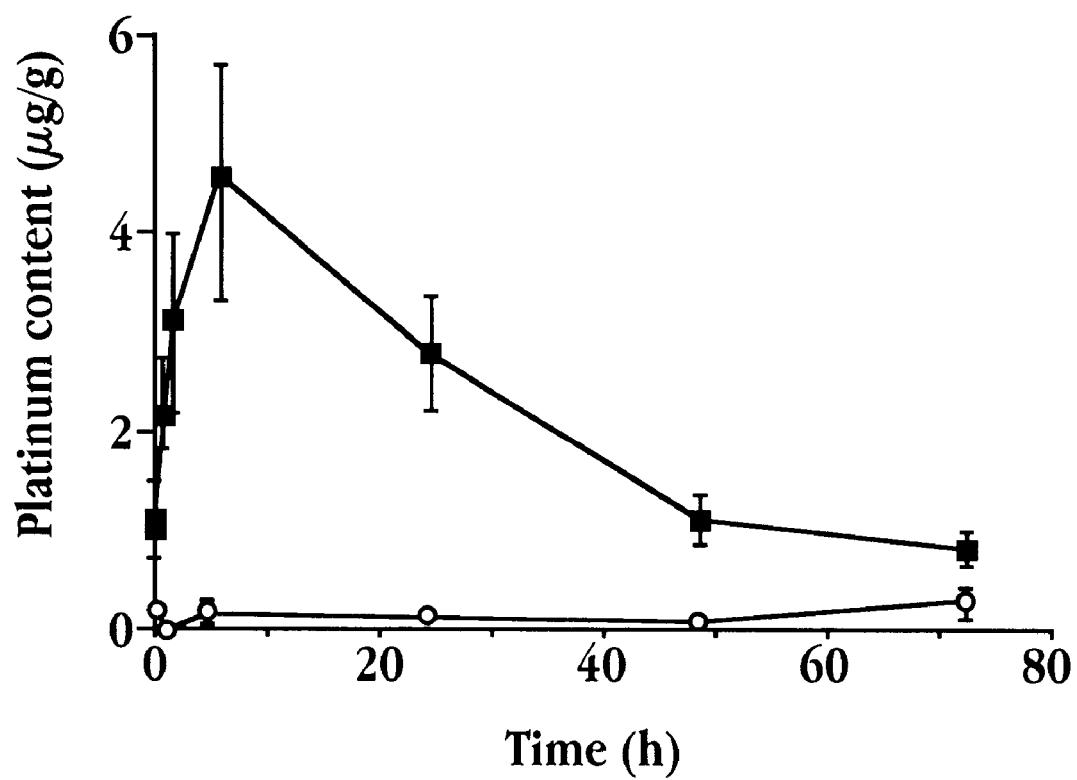
FIG. 13 is a plot showing platinum content, in μg/g, in tumors in mice after intravenous administration of HPMA copolymer-Gly-Phe-Leu-Gly-malonate-Pt (SEQ ID NO:10) (closed squares) or free cisplatin (open circles), as a function of time.

In another study, as described in Example 10, tumor-bearing mice were treated with HPMA copolymer-Gly-Phe-Leu-Gly-malonate-Pt (SEQ ID NO:10). The tumors were removed at intervals up to 72 hours after administration of the polymer-platinum compound and analyzed by AAS for platinum content. The results are shown in FIG. 13, and as seen, there is a significant difference in platinum content in mice treated with the polymer-platinum compound (closed squares) and in mice treated with free cisplatin (open circles). Four hours after administration of HPMA Copolymer-Gly-Phe-Leu-Gly-malonate-Pt (SEQ ID NO:10), a maximum in tumor platinum content was measured, this maximum being nearly 4-fold higher than the platinum present in the tumors of mice treated with free cisplatin. Clearly, the polymer-platinum compound of the invention is effective to accumulate in the tumor.

IV. Methods of Administering and Targeting the Polymer-Platinum Compounds

In another aspect, the invention includes a method of administering a platinum compound to a tumor in a subject. The method includes preparing a polymer-platinum compound having a polymer with platinum-containing oligopeptide side chains, as described above. The compound is administered to the tumor-bearing subject in a therapeutically effective amount.

For administration, the compound can be formulated in a variety of ways. For parenteral administration, the polymer-platinum compound is dissolved in an aqueous medium, e.g., isotonic saline, at a desired platinum concentration. The compound can be administered parenterally as a single bolus dose or as a slow infusion. Alternatively, the compound can be formulated for oral administration by preparation of tablets, elixirs, suspensions and the like.

Appropriate dosages for tumor treatment are determined based on the data presented herein for in vivo administration to tumor-bearing mice. This information, in combination with the known dosages for other platinum compounds, such as cisplatin and carboplatin, and the relationship is toxicity between these conventional platinates and the polymer-platinum compound of the present invention, provide guidance for selection of appropriate therapeutic dosages in humans. One skilled in the art could adjust dosing levels and regimens based on the differences in toxicity and/or pharmacokinetics of the known platinates with that of the polymer-platinum compounds to achieve even greater therapeutic advantage.

Chemotherapy using the polymer-platinum compounds of the present invention in combination with other chemotherapeutic agents may also be suitable for some types of cancers. For example, vinblastine, bleomycin, actinomycin, adriamycin, prednisone, vincristine, taxanes (taxotere, taxol), 5-fluorouracil, camptothecans, cyclophosphamide and gemcytobine can be administered in conjunction with the polymer-platinum compound. As an example, therapy of ovarian cancer may include administration of a therapeutically effective dosage of the polymer-platinum compound and adriamycin co-administered as a 24-hour infusion. It is further contemplated that other chemotherapeutic agents in development, such as topoisomerase inhibitors, angiogenesis inhibitors, can be administered in conjunction with the polymer-platinum compound.

In another aspect, the invention provides a method of enhancing the therapeutic index of a platinum species. The method includes complexing a platinum compound via a peptidyl side chain which terminates in a proximal end group for such attachment to achieve an enhanced therapeutic index, e.g., the ratio of the maximum tolerated dosage to the minimum curative dose. This is evidenced by the in vivo data discussed above, where the polymer-platinum complex was significantly less toxic than cisplatin yet was biologically active for tumor treatment.

In another aspect, the invention provides a method of targeting or selectively directing a greater percentage of the dosed materials to the tumor. As indicated above by example provided, platinum admininstered in the form of a polymer-platinum compound achieves greater accumulation in the tumor in relation to platinum compounds, and particularly platinate compounds, not complexed with a polymer.

From the foregoing, it can be appreciated how various features and objects of the invention are met. The polymer-platinum compound of the present invention is biocompatible, as evidenced by no cytotoxicity and no ability to lyse red blood cells. The platinum compound is attached to the polymer backbone via an oligopeptide side chain which is linked its distal end to the water-soluble, synthetic polymer and at its proximal end to the platinum compound. The rate of release of the attached platinum compound is controlled through selection of the composition and length of the side chain and the terminal end group on the side chain. The side chain in one embodiment is enzymatically biodegradable, providing a stable compound in the absence of suitable enzymes. In another embodiment, the side chain is non-enzymatically biodegradable and provides a more desirable release rate of platinum to achieve improved anti-tumor activity. The release rate of the platinum compound from the polymer-platinum compound can also be controlled by pH effects on both the composition and length of the oligopeptide side chain.

The anti-tumor activity achieved by the polymer-platinum complex of the present invention is due, at least in part, to the enhanced accumulation of the platinum compound at the tumor site. The composition and molecular weight of the polymer and of the oligopeptide side chain are factors effecting the accumulation and retention of the compound in tumors.

It will be appreciated that polymers other than HPMA are suitable for use in the polymer-platinum compound. As discussed above, the polymer for use in the compound is one which is biocompatible and which has a molecular weight sufficient for endothelial permeability at the tumor site and for removal from the body by renal clearance. For HPMA, the molecular weight threshold limiting glomerular filtration has been identified (Seymour, et al., 1987) at approximately 45,000 daltons. This threshold will differ, of course, for each polymer, depending on its physicochemical properties, and can be determined experimentally. For any polymer selected, the balance between endothelial permeability at the tumor site and removal by renal clearance mechanisms can be experimentally determined. The polymer further has physicochemical characteristics, e.g., solubility, stability, amenable to formulation in a pharmaceutically acceptable carrier and long-term storage.

EXAMPLES

The following examples illustrate preparation of the polymer-platinum compounds of the invention and characterization of the compounds. It will be appreciated that the Examples are illustrative and do not limit the invention in any way.

V. Materials

1. Chemicals

Cisplatin (cis-diamminedichloroplatinum(II)), potassium tetrachloroplatinate, o-phenylenediamine, ethylenediamine, diethylenetriamine, ninhydrin and hydrindantin were supplied by Sigma UK. Aminopropan-2-ol was supplied by Fluka. All solvents and chemicals were supplied by Sigma UK or Aldrich UK and were either distilled or dried over molecular sieves prior to use.

2. Cell Lines

The cell lines used, L132 (human embryonic lung cells), COR L23 (non-small cell lung cancer cells) and H69 (small cell lung cancer), were obtained from European Collection of Cell Cultures, Centre for Applied Biology, Microbiology and Research, Salisbury, Wiltshire UK.

VI. Methods

1. Atomic Absorption Spectroscopy (AAS)

Atomic absorption was performed using a (flame) Perkin-Elmer 280 instrument (Perkin-Elmer, Norwalk, Conn.) or a (flameless) Perkin Elmer AA100 (graphite furnace), calibrated with aqueous solutions of potassium tetrachloroplatinate ($K_2PtCl_4$) or cisplatin ($Pt(NH_3)_2Cl_2$) in concentrated nitric acid, concentrated hydrochloric acid, and hydrogen peroxide (30%).

2. o-Phenylenediamine Colorimetric Assay (o-PDA)

Samples containing 1–5 mg of unknown platinum content were dissolved in 1 ml double distilled water and 1 ml o-phenylenediamine (o-PDA) solution in dimethylformamide (DMF) (1–2 mg/ml) and incubated for 10 minutes at 100° C. The amount of platinum present in the sample was determined by measuring the absorbance at 703 nm using cisplatin as a reference.

Example 1

Synthesis of HPMA Copolymer-Peptide-Ethylenediamine

Synthesis of HPMA copolymers containing peptidyl-p-nitrophenol (ONp) has been described previously (Duncan, et al., 1987) the sections therein describing synthesis being herein incorporated by reference.

1 g of HPMA copolymer of weight average molecular weight (MW) of approximately 30,000 and polydispersity (Mw/Mn) of 1.3–1.5 containing pendant peptidyl sidechains, for example, Gly-Gly-ONp or Gly-Phe-Leu-Gly-ONp (SEQ ID NO:10) (5 mol % or 10 mol %), was added to 50 mL of double distilled water (DDW) and stirred at room temperature for 15 minutes or until dissolved. If necessary, the pH was adjusted to 5.7 with 0.01 M HCl.

The solution was added dropwise over 20 minutes to a stirring solution of ethylenediamine in 10 ml of DDW and then stirred for 4 hours. The mixture was filtered prior to a 4 day dialysis (visking tubing, pore size 10,000) against 5 L DDW. The resulting solution was concentrated to approximately 20 mL using Amicon "CENTRIPREP" filters (Amicon, Danvers, Mass.), pore size 10,000 and lyophilized yielding a white/off-white fluffy product (typical yield: 0.9 g).

The content of ethylenediamine in the product was determined by the ninhydrin method. Ninhydrin solution (1 ml, consisting of a solution of 20 g/L ninhydrin and 3 g/l hydrindantin in DMSO and sodium acetate buffer (pH 5.5) 75:25 v/v) was added to a 1 ml solution of sample and incubated at 75° C. for 15 minutes. The solution was allowed to stand for 15 minutes at room temperature prior to the addition of 3 ml ethanol solution (50 % v/v in DDW). The absorbance was recorded at 570 nm. The number of primary amino groups, calculated with reference to standard solutions prepared from 1-aminopropan-2-ol, for HPMA-Gly-Phe-Leu-Gly-ethylenediamine (SEQ ID NO:10) was 3–4× $10^{-4}$ mol/mg and for HPMA-Gly-Gly-ethylenediamine was 3–8×$10^{-4}$ mol/mg.

Example 2

Synthesis of HPMA Copolymer-Peptide-COONa

Synthesis of HPMA copolymers containing peptidyl-p-nitrophenol (ONp) has been described previously (Duncan, et al., 1987).

A solution of NaOH (0.01 M, 50 ml) was added to 1 g of HPMA copolymer of weight average MW of approximately 30,000 and polydispersity (Mw/Mn) of 1.3–1.5 containing pendant peptidyl sidechains, for example, Gly-Gly-ONp or Gly-Phe-Leu-Gly-ONp (SEQ ID NO:10) (5 or 10 mol %). The solution was stirred at room temperature for 4 hours prior to filtration and dialysis using a visking tubing, pore size 10,000 5 L DDW for 4 days. With filtration if necessary, the resulting solution was concentrated to 20 ml, using Amicon "CENTRIPREP" filters, pore size 10,000 and lyophilized yielding a white/off-white fluffy product (typical yield 0.9 g).

The following procedure was used to generate HPMA copolymer-Gly-Gly-OH and HPMA copolymer-Gly-Phe-Leu-Gly-OH (SEQ ID NO:10). A solution of HCl (0.02 M;

20 ml) was added to HPMA copolymer Gly-Gly-ONa or HPMA copolymer Gly-Phe-Leu-Gly-ONa (SEQ ID NO:10) (0.7 g) and the mixture stirred at room temperature for 4 hours before purification by centrifugation using an Amicon "CENTRIPREP" filter, pore size 10,000. The samples were spun at 2,000 g for 40 minutes until the filtered solution was colorless (minimum four spins). At each stage the polymer solution was diluted to 15 mL, with DDW before centrifugation. The resultant solution was lyophilized to give a fluffy white/off-white product (typical yield 0.5 g).

Quantitation of carboxylic acid groups was achieved by titrating a known concentration of sodium hydroxide with a known weight of the sample in a solution of DDW (acid-base titration). For HPMA-Gly-Phe-Leu-Gly-OH (SEQ ID NO:10), $2 \times 10^{-4}$ mol/g COOH groups were present, and for HPMA-Gly-Gly-OH, $3-5 \times 10^{-4}$ mol/g COOH groups were present.

Example 3

Biocompatibility of HPMA Copolymers

1. Cytotoxicity

Cells were cultured using standard conditions in microtitre plates. After 24 hours, seeding cells (typically L132 or B16 melanoma) at a density of $1 \times 10^6$ cells/ml the test polymers and poly-L-lysine (MW 56,500) as a positive reference were added at various concentrations (0–5 mg/ml). Cells were incubated for 72 hours prior to addition of 5-dimethylthiazol-2-yl-2,5-diphenyl tetrazolium bromide (MTT: 10 $\mu$l) to the culture medium. The plates were incubated for a further 5 hours, the medium was removed and 100 $\mu$l of dimethylsulfoxide (DMSO) was added to dissolve the dark blue crystals. Absorbance at 550 nm was measured using a microtitre plate reader and the viability of the test cultures was expressed as a percentage of control cells incubated in the absence of polymer.

2. Red Blood Cell Lysis

Blood was obtained from male Wistar rats after sacrifice by cardiac puncture. Erythrocytes were collected by centrifuging the blood three times in chilled phosphate buffered saline (PBS) at 4° C. at 1,000 g for 10 minutes. The final pellet was resuspended in PBS to give a 2% w/v solution of erythrocytes. Using a microtitre plate assay, 100 $\mu$l of the erythrocyte solution was added to about 100 $\mu$l of the test polymers at various concentrations and incubated for 5 hours. The detergent Triton X100 (1% v/v) used in one to produce 100% lysis. After incubation, the microtitre plates were centrifuged for 10 minutes at 1,000 g to sediment intact cells and the supernatants (100 $\mu$l) transferred into a new plate to determine hemoglobin release spectrophotometrically at 550 nm. Results, expressed as the amount of hemoglobin released as a percentage of the total (Triton X-100), are shown in FIG. 3.

Example 4

Synthesis of HPMA Copolymer-Gly-Phe-Leu-Gly-Ethylenediamine-Pt (SEQ ID NO:10) and HPMA-Gly-Gly-Ethylenediamine-Pt 1. Synthesis of HPMA-Gly-Phe-Leu-Gly-Ethylenediamine-Pt (SEQ ID NO:10)

To a solution of HPMA copolymer-Gly-Phe-Leu-Gly-ethylenediamine (SEQ ID NO:10) (from Example 1) (0.8 g in 20 ml, DDW) was added dropwise K$_2$[PtCl$_4$] in DDW over 20 minutes. Unbound platinum was removed by centrifugation (Amicon "CENTRIPREP" filters, pore size 10,000) spinning at 2,000×g for 40 minutes repeatedly (minimum 4 times) until the separated solution was colorless. The resultant solution containing polymer-platinum compound was diluted to 15 ml, with DDW at the beginning of each spin. The resulting polymer-platinum solution was lyophilized to yield a brown fluffy solid (typical yield 0.7 g). The reaction is illustrated in FIG. 4A.

The total platinum content was determined by atomic absorption spectroscopy or the o-PDA method as described above.

The results of typical analysis of several batches of HPMA co-polymer-Gly-Phe-Leu-Gly-ethylenediamine-Pt (SEQ ID NO:10) are shown in Table 4.

TABLE 4

| Sample No. | Total Pt by AAS (wt %) |
|---|---|
| 1 | 5.5 |
| 2 | 6.9 ± 1.63 |
| 3 | 10.1 ± 1.18 |
| 4 | 8.5 |
| 5 | 6.9 |

2. Synthesis of HPMA-Gly-Gly-ethylenediamine-Pt

To a solution of HPMA copolymer-Gly-Gly-ethylenediamine (from Example 1) (0.8 g in 20 mL DDW) was added dropwise K$_2$[PtCl$_4$] in DDW over 20 minutes. Unbound platinum was removed by centrifugation (Amicon "CENTRIPREP" filters, pore size 10,000) spinning at 2,000×g for 40 minutes repeatedly (minimum 4 times) until the separated solution was colorless. The resulting solution containing polymer-platinum was diluted to 15 ml, with DDW at the beginning of each spin. The centrifuged polymer-platinum solution was lyophilized to yield a brown fluffy solid (typical yield 0.7 g). The reaction is illustrated in FIG. 4B.

The total platinum content was determined by atomic absorption spectroscopy or the o-PDA method, as described above in the methods section. The results of typical analysis of several batches of HPMA copolymer Gly-Gly-ethylenediamine-Pt are shown in Table 5.

TABLE 5

| Sample No. | Total Pt by AAS (wt %) |
|---|---|
| 1 | 7 |
| 2 | 4.2 ± 1.4 |
| 3 | 8.59 ± 1.65 |
| 4 | 7.8 |

Example 5

Synthesis of HPMA Copolymer-Gly-Gly-O-Pt and HPMA Copolymer-Gly-Phe-Leu-Gly-O-Pt (SEQ ID NO:10)

Pt(NH$_3$)$_2$Cl$_2$ (0.12 g in 80 ml double distilled water) was added dropwise over 20 minutes to a solution of HPMA copolymer Gly-Gly-ONa (0.8 g in 30 ml DDW) under stirring at room temperature. The mixture was stirred for a further 4 hours. Unbound platinum was separated by centrifugation (Amicon "CENTRIPREP" filters, pore size 10,000) spinning at 2,000×g for 40 minutes repeatedly (minimum 4 times) until the separated solution was colorless. The resulting solution, typically 20 ml, was lyophilized to yield a white fluffy solid (typical yield 0.7 g). The reaction is illustrated in FIGS. 5A–5B.

The platinum content was determined by AAS and the o-PDA assay as described above.

The results of typical analysis of HPMA copolymer Gly-Gly-O-Pt and HPMA copolymer-Gly-Phe-Leu-Gly-O-Pt SEQ ID NO:10) are shown in Table 6.

TABLE 6

| Sample No. | Total Pt by AAS (wt %) |
|---|---|
| HPMA-Gly-Gly-O-Pt | |
| 1 | 2.0 |
| 2 | 2.1 |
| HPMA-Gly-Phe-Leu-Gly-O-Pt (SEQ ID NO:10) | |
| 1 | 7.7 |

Example 6

Synthesis of HPMA Copolymer-Gly-Phe-Leu-Gly-malonate-Pt (SEQ ID NO:10)

A solution of diethylaminomalonate hydrochloride (Compound XVII, 0.21 g in 2 ml anhydrous DMF) was added to a stirring solution of HPMA copolymer-Gly-Phe-Leu-Gly-ONp (SEQ ID NO:10) (Compound XVI, 0.5 g in 4 ml anhydrous DMF). Triethylamine (0.2 g) was then added over 4 minutes and the whole stirred for 15 hours. After evaporating to dryness under vacuum, the residue was dissolved in 4 ml of DDW. The solution was then filtered, applied to a 2.6×34 cm Sephadex G-25 column and eluted with DDW. The polymer fractions were combined and lyophilized to yield a fluffy white solid (Compound XVIII, 0.439 g). A 0.435 g portion of the solid was dissolved in 1.3 ml methanol. The solution was cooled to 15° C. and 0.686 ml of 0.99 M aqueous sodium hydroxide solution added, with stirring. After stirring at 15° C. for 15 minutes the stirring was continued at room temperature for a further 3.75 hours. The pH of the solution was adjusted to approximately 10.5 by the addition of 1 M hydrochloric acid and after filtering the solution was applied to a 2.6×34 cm Sephadex G-25 column and eluted with water. The polymer fractions (volume 60 ml) were combined and using Amicon "Centriprep 10" concentrators (MW cut-off 10,000 Daltons), concentrated to a volume of 20 ml (Amicon, Danvers, Mass.). The volume was made up, using double distilled water, to 45 ml and concentrated to 30 ml, made up to 45 ml and finally concentrated to 12 ml (repetitive ultrafiltration procedure). The pH of a 9 ml portion of the solution was adjusted to 7.5 using 0.01 M NaOH and the solution (Compound XIX) then added dropwise to 7.53 of cis-[Pt$(NH_3)_2(H_2O)_2$]$^{2+}$ solution, prepared as described below. The whole was stirred in the dark for 20 hours and then filtered. The filtrate was applied to a 2.6×34 cm Sephadex G-25 column and eluted with water. The polymer fractions were combined and lyophilized to yield a white fluffy solid (yield 0.206 g). The solid (Compound XX) was found to contain 9.9 wt % Pt (ICP analysis). The reaction scheme is illustrated in FIG. 6.

A. Preparation of the cis-[Pt$(NH_3)_2(H_2O)_2$]$^{2+}$ Solution

To a stirring suspension of cis-[PtCl$_2(NH_3)_2$] (0.2 g in 4 ml double distilled water) was added a solution of silver nitrate (0.221 g in 4 ml double distilled water). The mixture was stirred in the dark for 4 hours and then filtered. A set volume of the filtrate was used for platination purposes as indicated above.

Example 7A

In vitro Release of Pt from Polymer-Platinum Compounds

The polymer-platinum complexes prepared as described above in Examples 4 and 5, were dissolved in citrate phosphate buffer or phosphate buffered saline (PBS) at pH 5.5 and pH 7.4, respectively, and dialyzed against the respective solution at 37° C. Samples were taken regularly from the dialysate over 48 hours and free Pt analyzed using the o-PDA assay or by AAS as described above. The concentration of the Pt released from the polymer-platinum compounds was expressed as a percentage of the total available and results are shown in FIGS. 8A–8B.

Example 7B

In vitro Release of Pt from HPMA Copolymer-Gly-Phe-Leu-Gly-malonate-Pt (SEQ ID NO:10) (AAS Method)

The conjugate, prepared as described in Example 6, was dissolved in phosphate buffered saline, pH 7.4 (PBS) at 37° C. Samples of the solution were taken at 7 minutes, 4 hours, and 24 hours, and each applied to a Sephadex G-25 column. The column was eluted using PBS and the eluted fractions analyzed for Pt content by AAS. The amount of Pt released from the conjugate was expressed as a percentage of the total and the result is shown in FIG. 9A.

Example 7C

In vitro Release of Pt from HPMA Copolymer-Gly-Phe-Leu-Gly-malonate-Pt (SEQ ID NO:10) (o-PDA Method)

The conjugate, prepared as described above in Example 6, was dissolved in phosphate buffered saline, pH 7.4 and dialyzed (seamless visking cellulose tubing with a pore size of 2.4 nm and molecular weight cut of approximately 10,000) against the PBS solution at 37° C. Samples were taken regularly from the dialysate over 72 hours and free Pt analyzed using the o-Phenylenediamine colorimetric assay (o-PDA) carried out; samples containing unknown platinum content were added to 1 ml o-PDA solution in DMF (1.2 mg/ml) and incubated for 10 minutes at 100° C. The amount of platinum present in the sample was determined by measuring the absorbance at 704 nm using cisplatin as a reference. The concentration Pt released from the conjugate was expressed as a percentage of the total available and the result in shown in FIG. 9B.

Example 8

In Vivo Evaluation of Antitumor Activity and Toxicity

All animal studies were conducted according to the UKCCCR (United Kingdom Coordinating committee on Cancer Research) Guidelines.

I. L1210 i.p. Tumor Model $10^6$ viable cells were administered to $DBA_2$ mice (male 9–12 weeks, 20–30 g) i.p. on day 0. Animals were subsequently treated with either single or multiple i.p. doses on days 1, 2 and 3 with cisplatin or with the polymer-platinum compounds with HPMA-Gly-Phe-Leu-Gly-ethylenediamine-Pt (SEQ ID NO:10) or HPMA-Gly-Gly-ethylenediamine-Pt (prepared as described in Example 4). Animals were weighed daily and observed twice a day for signs of tumor progression and sacrificed if their body weight fell below 80% of the starting weight or if other severe toxicological problems were seen. At the end of the experiment changes in gross anatomy were noted. The results are shown in Table 2.

1. B16 Melanoma i.p. Model

Male C57BL/6J mice were inoculated with $10^6$ viable B16F10 cells intraperitoneally (i.p). The cells were injected on day 0 and free cisplatin or the polymer-platinum compound HPMA-Gly-Phe-Leu-Gly-ethylenediamine-Pt (SEQ ID NO:10) was injected as single or multiple doses i.p. on subsequent days. Animals were monitored as described above. The results are shown in Table 3.

2. B16 Melanoma s.c. Model

Male C57BL/6J mice were inoculated with $10^5$ viable B16F10 cells subcutaneously (s.c.). The tumor was allowed to establish until the area was approximately 50–70 $mm^2$, as measured by the product of two orthogonal diameters. Animals bearing s.c. tumors were treated by either i.p. or i.v. injection of free cisplatin or the polymer-platinum compounds HPMA-Gly-Phe-Leu-Gly-ethylenediamine-Pt (SEQ ID NO:10) and HPMA-Gly-Phe-Leu-Gly-O-Pt (SEQ ID NO:10) at 2, 5, 10, 15 mg Pt/kg.

The results are shown in FIG. 10A for the HPMA-Gly-Phe-Leu-Gly-ethylenediamine-Pt (SEQ ID NO:10) compound and in FIG. 10B for the HPMA-Gly-Phe-Leu-Gly-hydroxy-Pt compound (SEQ ID NO:10). The data are expressed as the ratio of the mean survival time of the treated animals divided by the mean survival of the untreated control group×100 (T/C).

Example 9

Biodistribution of HPMA Copolymer-Platinum Compounds

1. B16 Melanoma s.c. Model

Male C57BL/6J mice were inoculated with $10^5$ viable B16F10 cells s.c. and the tumor was allowed to establish until the area was approximately 50–70 $mm^2$ as measured by the product of two orthogonal diameters. Animals were injected i.v. with free cisplatin (1 mg/kg) or HPMA copolymer-Gly-Gly-ethylenediamine-Pt (1 mg/kg) and sacrificed at times up to 72 hours. The tumors were dissected and dissolved to give colorless solution using NaOH. Samples were analyzed using AAS to allow comparison of the Pt content of tumors taken from animals injected with free cisplatin and polymer-platinum complex. The results are shown in FIG. 12.

Example 10

Accumulation of HPMA Copolymer-Gly-Phe-Leu-Gly-malonate-Pt (SEQ ID NO:10) in Mice Bearing B15F10 Tumors Male C57B1/63 mice were inoculated with $10^5$ viable B16F10 cells s.c. and the tumor was allowed to establish until the area was approximately 50–70 $mm^2$ as measured by the product of two orthogonal diameters. Animals were injected i.v. with free cisplatin (1 mg/Kg) or HPMA Copolymer-Gly-Phe-Leu-Gly-malonate-Pt (SEQ ID NO:10) (1 mg/Kg) and animals sacrificed at times up to 72 hours. The tumors were removed, weighed and dissolved in nitric acid followed by hydrogen peroxide to give a colorless solution and subsequently made up to a known volume with water. Samples were analyzed using atomic absorption (flameless) spectroscopy that was performed using a Perkin-Elmer 280 instrument and calibration carried out with cisplatin ($Pt(NH_3)_2Cl_2$ in concentrated nitric acid, hydrogen peroxide (30%) and water. The results are shown in FIG. 13.

Although the invention has been described with respect to particular embodiments, it will be apparent to those skilled in the art that various changes and modifications can be made without departing from the invention.

---

It is claimed:

1. A composition for use in tumor treatment, comprising a polymer-platinum complex designed to accumulate at a tumor site and composed of an N-alkyl acrylamide polymer having side chains spaced along the polymer for complexing with a platinum compound, said side chains (i) composed of an oligopeptide attached at one end to the polymer and at the other end to the platinum compound and (ii) including at least one linkage which is designed to be cleaved under selected physiological conditions to yield the platinum compound which has, or is converted in vivo to have, anti-tumor activity.

2. The composition of claim 1, wherein said N-alkyl acrylamide polymer is a homopolymer having a molecular weight of between about 1,000–5,000,000 daltons.

3. The composition of claim 1, wherein said N-alkyl acrylamide polymer is a copolymer having a molecular weight between 1,000–5,000,000 daltons, said copolymer containing two repeat units m and n in a ratio m:n of between about 0.1–99.9.

4. The composition of claim 3, wherein said repeat units are composed of an N-alkyl acrylamide unit and of a unit carrying said oligopeptide side chain, said oligopeptide terminating in a proximal end group capable of attaching said platinum compound.

5. The composition of claim 4, which is a copolymer of the form:

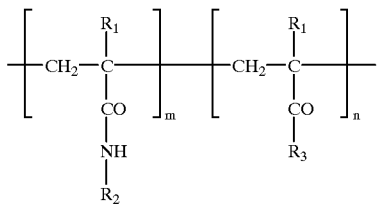

where $R_1$ is H or $CH_3$, $R_2$ is a lower alkyl or lower hydroxyalkyl group, and $R_3$ is the oligopeptide side chain.

6. The composition of claim 5, wherein said oligopeptide is selected from Gly-(W)$_p$-Gly where p is 0–3 and W is an amino acid or combination of any amino acids.

7. The composition of claim 5, wherein said oligopeptide is selected from the sequences identified as SEQ ID NO: 10 and SEQ ID NO: 1.

8. The composition of claim 5, wherein said proximal end group is selected from a carboxyl group, a diamine and a malonyl.

9. The composition of claim 5, wherein $R_1$ is $CH_3$, $R_2$ is 2-hydroxypropyl, and $R_3$ is Gly-Phe-Leu-Gly-[X] (SEQ ID NO:10) where [X] is selected from carboxyl, diamine and malonyl.

10. The composition of claim 5, wherein $R_1$ is $CH_3$, $R_2$ is 2-hydroxypropyl, and $R_3$ is SEQ ID NO:10 and the proximal end group is a diamine.

11. The composition of claim 1, wherein said polymer-platinum complex is dissolved in an aqueous medium suitable for parenteral administration.

12. A method of treating a solid tumor in a subject with a platinum compound, comprising preparing a polymer-platinum complex composed of an N-alkyl acrylamide polymer having side chains spaced along the polymer for complexing with a platinum compound, said side chains (i) composed of an oligopeptide attached at one end to the polymer and at the other end to the platinum compound and (ii) including at least one linkage which is designed to be cleaved under selected physiological conditions to yield the platinum compound which has, or is converted in vivo to have, anti-tumor activity; and parenterally administering a pharmaceutically effective amount of the complex to the subject.

13. The method of claim 12, wherein said N-alkyl acrylamide polymer is a homopolymer having a molecular weight of between about 1,000–5,000,000 daltons.

14. The method of claim 12, wherein said N-alkyl acrylamide polymer is a copolymer having a molecular weight between 1,000–5,000,000 daltons, said copolymer containing two repeat units m and n in a ratio m:n of between about 0.1–99.9.

15. The method of claim 14, wherein said repeat units are composed of an N-alkyl acrylamide unit and of a unit carrying said oligopeptide side chain, said oligopeptide terminating in a proximal end group capable of attaching said platinum compound.

16. The composition of claim 15, which is a copolymer of the form:

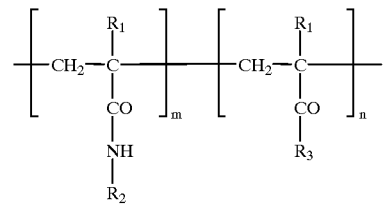

where $R_1$ is H or $CH_3$, $R_2$ is a lower alkyl or lower hydroxyalkyl group, and $R_3$ is the oligopeptide side chain.

17. The method of claim 16, wherein said oligopeptide is selected from Gly-(W)$_p$-Gly where p is 0–3 and W is an amino acid or combination of any amino acids.

18. The method of claim 16, wherein said oligopeptide is selected from the sequences identified as SEQ ID NO:10 and SEQ ID NO:1.

19. The method of claim 16, wherein said proximal end group is selected from a carboxyl group, a diamine and a malonyl.

20. The composition of claim 16, wherein $R_1$ is $CH_3$, $R_2$ is 2-hydroxypropyl, and $R_3$ is Gly-Phe-Leu-Gly-[X] (SEQ ID NO:10) where [X] is selected from the group consisting of carboxyl, diamine and malonyl.

21. The method of claim 16, wherein $R_1$ is $CH_3$, $R_2$ is 2-hydroxypropyl, and $R_3$ is SEQ ID NO:10 and the proximal end group is a diamine.

22. A method of enhancing the therapeutic index of a platinum compound, when the compound is used for treating a tumor by administering parenterally a pharmaceutically acceptable solution containing the compound to a subject, comprising prior to said administering, complexing the platinum compound with a copolymer composed of an N-alkyl acrylamide first repeat unit and a second repeat unit having an oligopeptide side chain which terminates in a proximal end group capable of complexing with said platinum compound.

23. A method of improving the solubility of a platinum compound comprising complexing the compound with a copolymer composed of an N-alkyl acrylamide first repeat unit and a second repeat unit having an oligopeptide side chain which terminates in a proximal end group capable of complexing with said platinum compound.

24. A method of improving the stability of a platinum compound comprising complexing the compound with a copolymer composed of an N-alkyl acrylamide first repeat unit and a second repeat unit having an oligopeptide side chain which terminates in a proximal end group capable of complexing with said platinum compound.

* * * * *